(12) United States Patent
Gallagher et al.

(10) Patent No.: US 12,145,534 B2
(45) Date of Patent: Nov. 19, 2024

(54) METHOD AND APPARATUS FOR MONITORING STATUS OF PERSONS IN A VEHICLE

(71) Applicant: ATSR LIMITED, Tullamore (IE)

(72) Inventors: Eric Gallagher, Ballyshannon (IE);
Valdas Bockus, Crinkle (IE); Colm Loughnane, Birr (IE)

(73) Assignee: ATSR LIMITED, Tullamore (IE)

( * ) Notice: Subject to any disclaimer, the term of this patent is extended or adjusted under 35 U.S.C. 154(b) by 369 days.

(21) Appl. No.: 17/442,427

(22) PCT Filed: Mar. 26, 2020

(86) PCT No.: PCT/EP2020/058631
§ 371 (c)(1),
(2) Date: Sep. 23, 2021

(87) PCT Pub. No.: WO2020/193738
PCT Pub. Date: Oct. 1, 2020

(65) Prior Publication Data
US 2022/0161808 A1 May 26, 2022

(30) Foreign Application Priority Data

Mar. 26, 2019 (GB) .................................... 1904149

(51) Int. Cl.
*G06V 40/10* (2022.01)
*A61B 5/01* (2006.01)
(Continued)

(52) U.S. Cl.
CPC .............. *B60R 25/305* (2013.01); *A61B 5/01* (2013.01); *A61G 3/061* (2013.01); *A61G 3/062* (2013.01);
(Continued)

(58) Field of Classification Search
None
See application file for complete search history.

(56) References Cited

U.S. PATENT DOCUMENTS 10,072,453 B2 9/2018 Ihlenburg et al.
10,139,827 B2 11/2018 Charette et al.
(Continued)

FOREIGN PATENT DOCUMENTS

CN 2680523 Y 2/2005
CN 108743069 A 11/2018
(Continued)

OTHER PUBLICATIONS

Great Britain Combined Search and Examination Report dated Aug. 8, 2019 which was issue in connection with GB1904149.0.
(Continued)

*Primary Examiner* — Amelia Vorce
(74) *Attorney, Agent, or Firm* — Buckley, Maschoff & Talwalkar LLC

(57) ABSTRACT

The present disclosure relates to a method and system for monitoring the status of a person in the vicinity of a vehicle, including capturing an image of an area in the vehicle or in the vicinity of the vehicle, analysing the captured image, detecting if the captured image contains a person, determining at a first time a characteristic associated with the person in the captured image, comparing the characteristic with a predefined threshold value; and in response to the determined parameter surpassing the predefined threshold value, actuating a change of state of the vehicle. The characteristic may comprise temperature.

14 Claims, 30 Drawing Sheets

(51) Int. Cl.

| | |
|---|---|
| *A61G 3/06* | (2006.01) |
| *B60R 25/102* | (2013.01) |
| *B60R 25/104* | (2013.01) |
| *B60R 25/24* | (2013.01) |
| *B60R 25/25* | (2013.01) |
| *B60R 25/30* | (2013.01) |
| *B60R 25/31* | (2013.01) |
| *B60W 50/00* | (2006.01) |
| *B60W 50/14* | (2020.01) |
| *G06T 7/00* | (2017.01) |
| *G06T 7/70* | (2017.01) |
| *G06V 10/70* | (2022.01) |
| *G06V 20/52* | (2022.01) |
| *G06V 20/56* | (2022.01) |
| *G06V 20/58* | (2022.01) |
| *G06V 20/59* | (2022.01) |
| *G08B 13/196* | (2006.01) |
| *H04N 5/76* | (2006.01) |
| *H04N 7/18* | (2006.01) |

(52) U.S. Cl.
CPC .......... *B60R 25/102* (2013.01); *B60R 25/104* (2013.01); *B60R 25/24* (2013.01); *B60R 25/25* (2013.01); *B60R 25/302* (2013.01); *B60R 25/31* (2013.01); *B60W 50/0098* (2013.01); *B60W 50/14* (2013.01); *G06T 7/0008* (2013.01); *G06T 7/70* (2017.01); *G06V 10/70* (2022.01); *G06V 20/52* (2022.01); *G06V 20/56* (2022.01); *G06V 20/58* (2022.01); *G06V 20/59* (2022.01); *G06V 40/10* (2022.01); *G08B 13/19647* (2013.01); *H04N 5/76* (2013.01); *H04N 7/188* (2013.01); *G06T 2207/30196* (2013.01); *G06T 2207/30242* (2013.01); *G06T 2207/30268* (2013.01)

(56) References Cited

U.S. PATENT DOCUMENTS

| | | | |
|---|---|---|---|
| 10,152,870 B1 | 12/2018 | Williams et al. | |
| 2009/0027493 A1 | 1/2009 | Amar et al. | |
| 2010/0298661 A1* | 11/2010 | McCombie | A61B 5/7278 |
| | | | 600/587 |
| 2013/0125468 A1 | 5/2013 | El Fassi et al. | |
| 2014/0112537 A1* | 4/2014 | Frank | G01N 21/17 |
| | | | 315/149 |
| 2014/0306826 A1* | 10/2014 | Ricci | G01C 21/26 |
| | | | 340/573.1 |
| 2015/0038855 A1* | 2/2015 | Berckmans | A61B 5/02055 |
| | | | 600/483 |
| 2016/0363340 A1* | 12/2016 | Shikii | F24F 11/74 |
| 2017/0036541 A1* | 2/2017 | Brankovic | A61B 5/6893 |
| 2017/0166164 A1 | 6/2017 | Sticherling et al. | |
| 2018/0160057 A1* | 6/2018 | Newman | G07C 5/008 |
| 2018/0268237 A1* | 9/2018 | Stanimirovic | G06T 7/248 |
| 2019/0019384 A1 | 1/2019 | Maksuti | |
| 2019/0049968 A1* | 2/2019 | Dean | A61G 5/04 |
| 2019/0146500 A1* | 5/2019 | Yalla | G06F 16/29 |
| | | | 701/25 |
| 2019/0197414 A1* | 6/2019 | Zerick | G16H 10/60 |
| 2019/0279447 A1* | 9/2019 | Ricci | A61B 5/4809 |
| 2020/0202693 A1* | 6/2020 | Aoyama | H04N 7/188 |
| 2020/0256581 A1* | 8/2020 | Wang | F24F 11/64 |
| 2021/0110692 A1* | 4/2021 | Alpert | G08B 26/008 |
| 2022/0045554 A1* | 2/2022 | Leabman | A61B 8/56 |
| 2022/0175265 A1* | 6/2022 | Watts | A61B 5/445 |

FOREIGN PATENT DOCUMENTS

| | | | | |
|---|---|---|---|---|
| CN | 109481160 A | | 11/2018 | |
| DE | 102017218100 A1 | | 4/2019 | |
| JP | 2005315024 A | | 11/2005 | |
| JP | 2016079692 A | | 5/2016 | |
| WO | 2004012140 A2 | | 2/2004 | |
| WO | 2011116836 A1 | | 9/2011 | |
| WO | 2011137057 A1 | | 11/2011 | |
| WO | WO-2012073016 A1 | * | 6/2012 | ............ A61B 3/113 |
| WO | 2015113549 A1 | | 8/2015 | |
| WO | 2017155448 A1 | | 9/2017 | |
| WO | 2019040929 A1 | | 2/2019 | |

OTHER PUBLICATIONS

International Search Report and Written Opinion dated Jan. 31, 2020 which was issued in connection with PCT/EP2020/058631.
International Search Report and Written Opinion dated Jun. 19, 2020 which was issued in connection with PCT/EP2019/079302.
International Search Report and Written Opinion dated Jan. 31, 2020 which was issued in connection with PCT/EP2019/079308.
International Search Report and Written Opinion dated Jan. 31, 2020 which was issued in connection with PCT/EP2019/079309.
International Search Report and Written Opinion dated Jun. 19, 2020 which was issued in connection with PCT/EP2020/058628.

* cited by examiner

METHOD AND APPARATUS FOR MONITORING STATUS OF PERSONS IN A VEHICLE

FIELD OF THE INVENTION

The present invention relates to a method and system for monitoring the status of persons in a vehicle.

BACKGROUND OF THE INVENTION

Biometric identification has found a large number of applications in recent years, and particularly in the field of security. The uniqueness of human features, whether that is facial features (such as facial structure or eyes), finger prints or hand prints, adds a level of security vastly more difficult to "hack" than historical conventional security means such as password identification. Typically optical sensors of various kinds are used to detect unique facial features among other biometric markers which identify an individual for authorisation/security clearance.

A common scenario in the field of emergency response medical treatment is one in which paramedics are treating and collecting patients at a scene containing at least one or several sources of threat to themselves the patient and the ambulance vehicle itself, for example, a riot or terrorist incident or the like). The risk of vehicle hijacking is a very real possibility in such a scenario if the paramedic(s) should forget to lock the ambulance upon leaving it to attend a patient or upon returning to the vehicle. Moreover, paramedics are required by law to leave vehicles running at the scene, making hijacking an even more realistic threat.

In addition to improving security, providing automated access to the clinical environment of the ambulance—for example via a ramp, lift or other means—is desirable to reduce the risk of an accident occurring during the loading of a patient in to the ambulance, and to reduce the time between approaching the ambulance and driving away, in a high-stress environment. Such a scenario also presents an increased risk of incorrect patient harnessing or positioning.

Furthermore, the regulation of environment parameters on board the ambulance-parameters which ideally are tailored to the condition of the patient such as temperature, pressure and humidity—is a step which might go amiss in such a high-stress scenario. Moreover, versatility of the ambulance service ought to be a priority given the demand for ambulances worldwide in locations varying for example in temperature and altitude. Response external environment conditions may differ globally as much as a dry desert at sea-level with 50° C., a sub-polar environment at −40° C. or a high elevation environment e.g. 10,000 ft above sea-level. In any such environment it is crucial that the patient is introduced to an environment which is determined to not be adverse to their health and their treatment. For example, a patient suffering from severe heatstroke would benefit from a cool environment or an environment which is gradually brought to a cool temperature with respect to the external environment. The above description is to at least some extent equally applicable for other emergency response vehicles such as an emergency helicopter or an emergency boat.

It is thus desirable to provide a method and apparatus for controlling access to a vehicle which addresses at least some of the drawbacks of the prior art.

SUMMARY OF THE INVENTION

According to a first aspect of the invention there is provided a method for controlling access to a vehicle, comprising:

capturing an image of an area in the vicinity of the vehicle;

analysing the captured image;

detecting if the captured image contains both at least one person and a personnel transport apparatus;

determining if the at least one person in the captured image is authorised to access the vehicle;

determining a type of personnel transport apparatus and controlling a parameter of the vehicle in response to the determined type; and selectively controlling a locking mechanism of the vehicle in response to the captured image containing at least one authorised person and the personnel transport apparatus.

Advantageously, the method further comprises determining if the personnel transport apparatus is a stretcher, a wheelchair or a dolly.

Further advantageously, the method comprises determining the type of the stretcher, the type of the wheelchair or the type of the dolly.

Advantageously, the method further comprises determining which means of access to the vehicle is substantially suitable for accessing the vehicle based on the type of the personnel transport apparatus in the captured image.

Advantageously, the method further comprises extending a ramp from the vehicle to facilitate access of the personnel transport apparatus to the vehicle in response to the type of personnel transport apparatus.

Advantageously, the method further comprises lowering a lift to facilitate access of the personnel transport apparatus to the vehicle.

Beneficially, the method further comprises selectively controlling at least one parameter of the vehicle in response to detecting both of the at least one authorised personnel and the personnel transport apparatus approaching the vicinity of the vehicle.

Preferably, the at least one parameter is an environmental parameter.

Advantageously the environmental parameter comprises temperature.

Advantageously, the method further comprises measuring at least one external environment parameter of the vehicle.

Advantageously, the method further comprises controlling a vehicle environment parameter in response to the at least one measured external environment parameter.

Advantageously, the method further comprises regulating the vehicle environment to a predefined characteristic.

Advantageously, the method further comprises detecting if a person on the personnel transport apparatus is correctly harnessed according to a predefined protocol.

Advantageously, the method further comprises detecting if a person on the personnel transport apparatus is correctly positioned on said personnel transport apparatus according to a predefined protocol.

Advantageously, the method further comprises maintaining a log in memory each time the predefined protocol was breached.

Preferably the log in memory is associated with a user profile of one or more authorised personnel.

Advantageously, the method further comprises transmitting at least part of the contents of the memory to a remote database.

Ideally a transmission transmits at least part of the contents of the memory to a remote database when the predefined protocol was breached.

Preferably the transmission is a wireless transmission.

Advantageously, the method further comprises providing an audio and/or visual notification from the vehicle detailing which means of access to the vehicle is substantially suitable for accessing the vehicle based on the type of the personnel transport apparatus in the captured image.

Advantageously, the method further comprises determining whether the type of the personnel transport apparatus in the captured image is an authorised type of personnel transport apparatus.

According to a second aspect of the invention there is provided a method for controlling access to a vehicle, the method comprising:
 capturing an image of an area in the vicinity of the vehicle;
 analysing the captured image;
 detecting if the captured image contains a personnel transport apparatus;
 determining a type of personnel transport apparatus and controlling a parameter of the vehicle in response to the determined type; and
 selectively controlling a locking mechanism of the vehicle in response to the captured image containing the personnel transport apparatus.

Preferably the method further comprises determining which means of access to the vehicle is substantially suitable for accessing the vehicle based on the type of the personnel transport apparatus in the captured image.

According to third aspect of the invention there is provided an apparatus for controlling access to a vehicle, comprising:
 an image capture device for capturing an image of an area in the vicinity of the vehicle;
 an image analysing means for analysing the captured image;
 a detecting means for detecting if the captured images contain both at least one person and a personnel transport apparatus, wherein the detecting means is further configured for determining the type of the personnel transport apparatus;
 a processing means for determining if the at least one person in the captured image is authorised to access the vehicle; and
 a control means for selectively controlling a locking mechanism of the vehicle in response to the captured image containing at least one authorised person and the personnel transport apparatus.

Preferably the processing means is configured to implement a machine learning algorithm.

Further preferably the detecting means is configured for detecting if the personnel transport apparatus is a stretcher, a wheelchair or a dolly.

Ideally the detecting means is configured for detecting the type of the stretcher, the type of the wheelchair or the type of the dolly.

Preferably the control means is further configured for controlling operations of a mechanical apparatus associated with the vehicle.

In one aspect the mechanical apparatus is a retractable ramp.

In another aspect the mechanical apparatus is a lift.

Preferably the apparatus further comprises an environment measurement means for measuring one or more vehicle environment parameters.

Further preferably the apparatus further comprises an environment controlling means for controlling one or more vehicle environment parameters.

Ideally the apparatus further comprises an external environment measurement means for measuring one or more external environment parameters.

Preferably the apparatus further comprises memory for storing one or more environment control protocols defining instructions for controlling the vehicle environment parameters.

Beneficially the control means is configured for varying the one or more environment parameters towards predefined values for the one or more environment parameters, with respect to the external environment parameters.

Further beneficially the control means is configured for dynamically adjusting power output of the environment controlling means in dependence on one or a combination of one or more environment parameters, one or more external environment parameters, duration the vehicle doors have been open and duration of presence of the at least one authorised personnel in the vicinity of the vehicle.

Preferably the control means is operationally associated with the vehicle electromechanical actuators.

Preferably the image analysing means is configured to determine if one or both of said at least one authorised personnel and a person on the personnel transport apparatus are correctly harnessed according to a predefined protocol.

Further preferably the image analysing means is configured to determine if a person on the personnel transport apparatus is correctly positioned according to a predefined protocol.

Ideally the apparatus further comprises memory for storing one or more predefined protocols for harnessing and/or positioning a person on the patient transport apparatus.

Further ideally the apparatus further comprises a communication means for communicating with a remote server or a remote database.

Preferably the communication means is a wireless communication means.

Preferably the control means is configured for locking the vehicle doors if a predefined combination or number of authorised personnel leaves the vehicle or the vicinity of the vehicle.

Preferably the apparatus further comprises a recording means for synchronously recording personnel status, vehicle environment and vehicle parameter data.

Advantageously the detecting means is configured for detecting fluid spillage.

In one aspect the fluid is a bodily fluid including but not limited to blood or vomit.

Advantageously the apparatus further comprises memory for storing one or more of synchronously recorded data, harnessing protocol adherence, positioning protocol adherence and fluid spillage.

Ideally the processing means is further configured to generate a report to be transmitted wirelessly to a remote server or a remote database.

Preferably the report to be transmitted to a remote server or a remote database contains one or more of the synchronously recorded data, harnessing protocol adherence, positioning protocol adherence and fluid spillage.

Advantageously, the detecting means is further configured to determine the distance of the at least one person and one or more objects from the vehicle, their duration of time from the vehicle, and the direction and speed of their motion with respect to the vehicle.

Advantageously, the apparatus further comprises a notification means configured for providing an audio and/or visual notification.

According to a fourth aspect of the invention there is provided a computer-readable medium comprising instructions which, when executed, cause a processor to carry out one or more aspects of a method as those outlined above.

According to a fifth aspect of the invention there is provided an emergency vehicle comprising the apparatus of the second and third aspects.

In a further aspect of the invention there is provided a method of monitoring the status of a person in a vehicle. The method comprises the steps of:
- capturing an image of an area in the vicinity of the vehicle;
- analysing the captured image;
- detecting if the captured image contains a person;
- determining at a first time a characteristic associated with the person in the captured image;
- comparing the characteristic with a predefined threshold value; and
- in response to the determined parameter surpassing the predefined threshold value, actuating a change of state of the vehicle.

A system for implementing the method of monitoring the status of a person in a vehicle is also provided. The system comprises:
- an image capture device configured for capturing an image of an area in the vicinity of a vehicle;
- an image analysing means configured for analysing the captured image, wherein the image analysing means is configured for detecting a person in the captured image, wherein the image analysing means is further configured to determine a characteristic associated with the person;
- memory storing one or more predefined threshold values; and
- a processor, wherein the processor is configured to compare the determined characteristic with a predefined threshold value, wherein the processor is configured to actuate a change of state of the vehicle in response to the determined characteristic surpassing the predefined threshold value.

DETAILED DESCRIPTION OF THE DRAWINGS

The present teaching will now be described with reference to an exemplary method and apparatus. It will be understood that the exemplary method and apparatus are provided to assist in an understanding of the present teaching and are not to be construed as limiting in any fashion. Furthermore, elements or components that are described with reference to any one Figure may be interchanged with those of other Figures or other equivalent elements without departing from the spirit of the present teaching.

Referring now to the Figures there is illustrated a method and apparatus for controlling access to a vehicle, wherein when at least one authorised person and a patient transport apparatus are detected by optical sensors the state of a locking mechanism of the vehicle can be switched to the 'open' state. In the exemplary embodiment, the vehicle is an ambulance. It will be understood that the description of the present disclosure can equally apply to any vehicle appropriately outfitted with the relevant components and the apparatus herein. Moreover, where in the exemplary embodiment 'ambulance' is used in place of 'vehicle', for consistency in the context the term 'paramedic' will replace 'person' and ought to be understood as referring to an authorised personnel. Unauthorised personnel are referred to as 'further person(s)'. It will be understood that in embodiments involving any vehicle appropriately outfitted with the relevant components and the apparatus herein, the term 'person' may be used. What is more, whilst the term 'patient transport apparatus' is generally used herein, it will be understood that since the disclosure is not isolated to an ambulance the use of the word 'patient' is not always most appropriate. For example, a more general term may be 'personnel transport apparatus'. This may cover, by way of example only, contexts in which the vehicle is a police vehicle, security vehicle, military vehicle, fire engine or the like, as well as a civilian vehicle.

Figure 1:
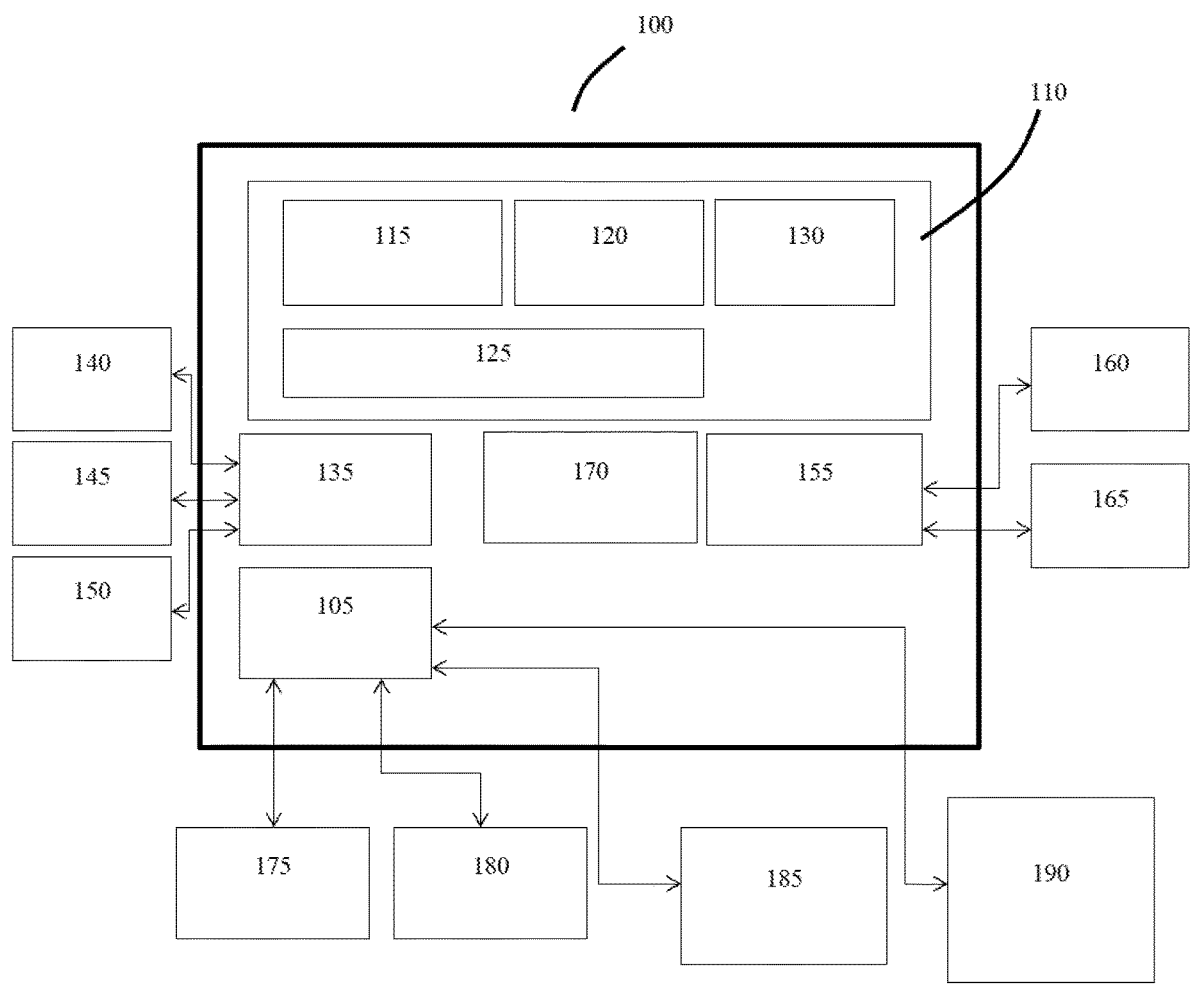
FIG. 1 is an illustration of an apparatus according to an embodiment of the present disclosure.

FIG. 1 is a block diagram illustrating a configuration of an apparatus comprising a computing device 100 which includes various hardware and software components that, in conjunction with a plurality of external devices it is operationally associated with, function to perform processes according to the present disclosure. Referring to FIG. 1, the computing device 100 comprises a processor/processing means 105 in communication with memory 110. The processor 105 functions to execute software instructions that can be loaded and stored in the memory 110. The processor 105 may include a number of processors, a multi-processor core, or some other type of processor, depending on the particular implementation. The memory 110 may be accessible by the processor 105, thereby enabling the processor 105 to receive and execute instructions stored on the memory 110. The memory 110 may be, for example, a random access memory (RAM) or any other suitable volatile or non-volatile computer readable storage medium. In addition, the memory 110 may be fixed or removable and may contain one or more components or devices such as a hard drive, a flash memory, a rewritable optical disk, a rewritable magnetic tape, or some combination of the above.

One or more software modules may be encoded in the memory 110. The software modules may comprise one or more software programs or applications having computer program code or a set of instructions configured to be executed by the processor 105. Such computer program code or instructions for carrying out operations for aspects of the systems and methods disclosed herein may be written in any combination of one or more programming languages.

The software modules may include at least a first application 115 configured to be executed by the processor 105. The software modules may further include a second application 120 and a third application 125 configured to be executed by the processor 105. During execution of the software modules, the processor 105 configures the computing device 100 to perform various operations relating to the embodiments of the present disclosure, as will be described below. In the exemplary embodiment, the first, second and third applications 115, 120 and 125 may be an image analysing means 115, a detection means 120 and a recording means 125.

Image analysis will be understood to entail a multitude of techniques known to one skilled in the art, including but not limited to one or more of digital signal processing, Fourier analysis and 3D pose estimation. The detecting means 120 may comprise any software package for detecting specific features of an image: it will be understood that this may entail edge detection software; one or more machine learning techniques such as deep learning algorithms implementing neural networks: pattern recognition and feature detection. These techniques may be implemented once on any single frame or dynamically on a live feed comprising a plurality of frames.

Other information and/or data relevant to the operation of the present apparatus, systems and methods, such as a database 130, may also be stored on the memory 110. The database 130 may contain and/or maintain various data items and elements that are utilized throughout the various operations of the apparatus and system described below. It should be noted that although the database 130 is depicted as being configured locally to the computing device 100, in certain implementations the database 130 and/or various other data elements stored therein may be located remotely. Such elements may be located on a remote device or server—not shown, and connected to the computing device 100 through a network in a manner known to those skilled in the art, in order to be loaded into a processor and executed.

Further, the program code of the software modules and one or more computer readable storage devices (such as the memory 110) form a computer program product that may be manufactured and/or distributed in accordance with the present disclosure, as is known to those of skill in the art.

A control means 135 may be operationally associated with the processor 105. The control means 135 may be further operationally associated with one or further external devices 140, 145, 150. In the exemplary embodiment, the control means 135 may be operationally associated with a vehicle locking mechanism 140, a vehicle ramp/lift mechanism 145 and vehicle electromechanical actuators 150. The vehicle electromechanical actuators 150 will be understood by the skilled person to comprise, but is not limited to, the electromechanical sensor(s), actuator(s) and circuit(s) which may be found on-board a vehicle.

A communication means 155 is also operatively connected to the processor 105 and may be any interface that enables communication between the computing device 100 and other devices, machines and/or elements. The communication means 155 is configured for transmitting and/or receiving data from remote databases 160 and/or servers 165. For example, the communication means 155 may include but is not limited to a Bluetooth, or cellular transceiver, a satellite communication transmitter/receiver, an optical port and/or any other such, interfaces for wirelessly connecting the computing device 100 to the other devices.

A user interface 170 is also operatively connected to the processor 105. The user interface 170 may comprise one or more input device(s) such as switch(es), button(s), key(s), and a touchscreen.

The user interface 170 functions to facilitate the capture of commands from the user such as on-off commands or settings related to operation of the apparatus and system described below: The user interface 170 may function to issue remote instantaneous instructions or notifications on images received via a non-local image capture mechanism.

The processor 105 may be further operationally associated with one or more external devices. The one or more external devices may include but are not limited to an image capture device 175, an environment control means 180, an environment measurement means 185 and an external environment measurement means 190. Data may be transmitted to and/or from these external devices. Data from these external devices may be processed by the processor 105 implementing one or more of the software packages stored in memory 110. Data from the external devices may be stored in memory 110 via the recording means 125. Instructions such as predefined protocols stored in memory 110 may be sent to the external devices via the processor 105.

The computing device 100 may further be associated with one or more further computing devices 100 in an Internet of Things (IoT) network, using the communication means 155 on-board every computing device 100. The IoT network may comprise one or more remote server(s) and remote database(s), and software modules located locally to any number of computing devices 100 or located remotely on said remote server(s) and/or database(s). The software modules may comprise means to process data received from one or more computing devices 100 and may be configured to produce virtual models to optimise parameters associated with said one or more computing devices 100.

Figure 2:
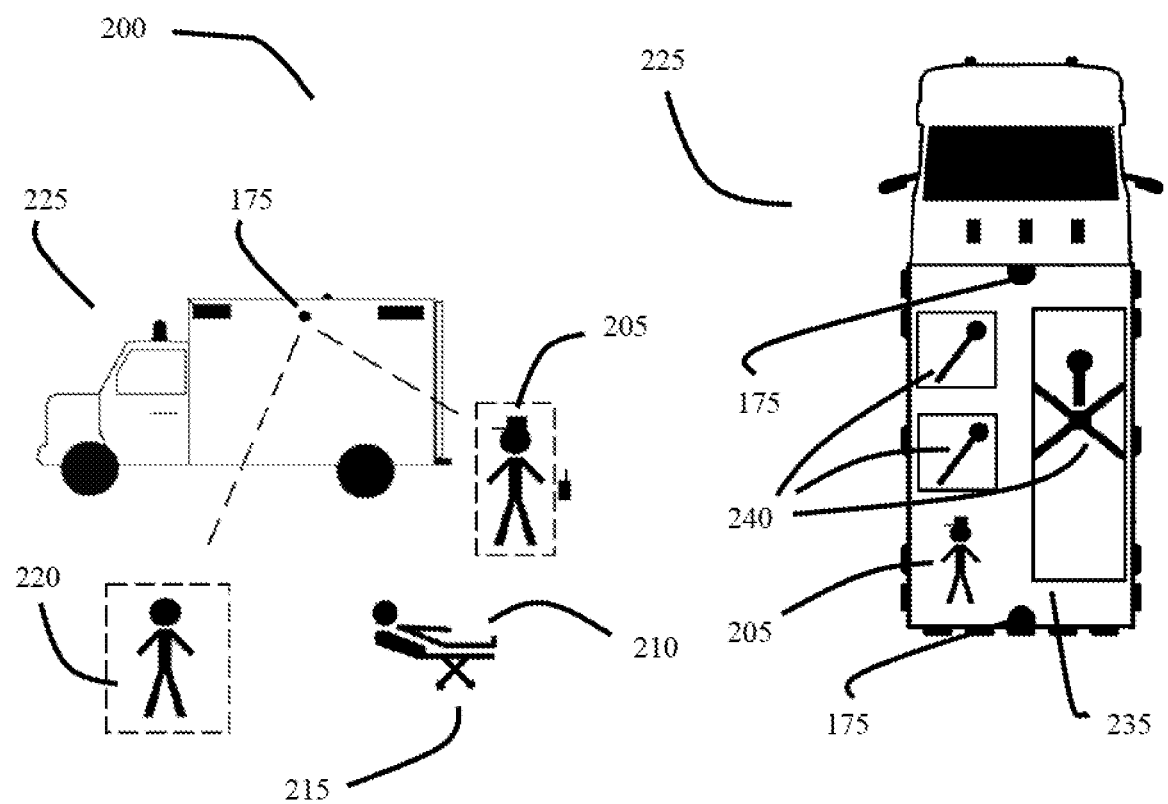
FIG. 2 is an illustration of elevation and plans views of a scenario in which the apparatus may be implemented according to an embodiment of the present disclosure.

FIG. 2 illustrates an elevation view of a common scenario 200 in the work of an emergency medical response unit. A paramedic 205 attends to a patient 210 and loads the patient 210 on to a patient transport apparatus 215. In one embodiment, the patient transport apparatus 215 is a stretcher. In another embodiment, the patient transport apparatus 215 is a wheelchair. In a further embodiment the patient transport apparatus 215 is a dolly. At least one further person 220 who is not a member of the ambulance staff is typically also present at the scene. Once the patient 210 is deemed by the paramedic 205 to be secure on board the patient transport apparatus 215, the paramedic 205 will seek to load the patient 210 on to the ambulance 225 via the rear doors.

As discussed above, the work of a paramedic may entail arriving at a scene with multiple threats, such as during a riot or terrorist incident. For example, the further person(s) 220 may be rioter(s) or terrorist(s) who pose a threat to the paramedic 205, the patient 210 and the surrounding population proper. The further person(s) 220 may seek to hijack the vehicle, and may be successful if the paramedic 205 forgets to lock the ambulance doors when leaving the ambulance 225. To provide a layer of security against this, detection and biometric authorisation of the paramedic 205 leaving the ambulance 225 may actuate locking of the doors. When returning, detection and biometric authorisation of the paramedic 205 together with detection of the patient transport apparatus 215 may be implemented to unlock the ambulance doors according to the embodiments of the present disclosure. Being able to control access to an ambulance on the basis of biometric authorisation of ambulance personnel, and additionally detection of a patient transport apparatus, adds a layer of security which greatly diminishes the chance of a hijacking occurring.

The image capture device 175 may capture an image of an area in the vicinity of the ambulance 225. In one embodiment, the image comprises a single frame. In another embodiment, the image comprises a plurality of frames. In a further embodiment, the image comprising a plurality of frames may form a video. The image capture device 175 may be placed on top of the ambulance 225 or on one of its vertical sidewalls. The image capture device 175 may be a singular camera or a multitude of cameras positioned together as an array or strategically at various points on the body of the ambulance 225.

Figure 4:
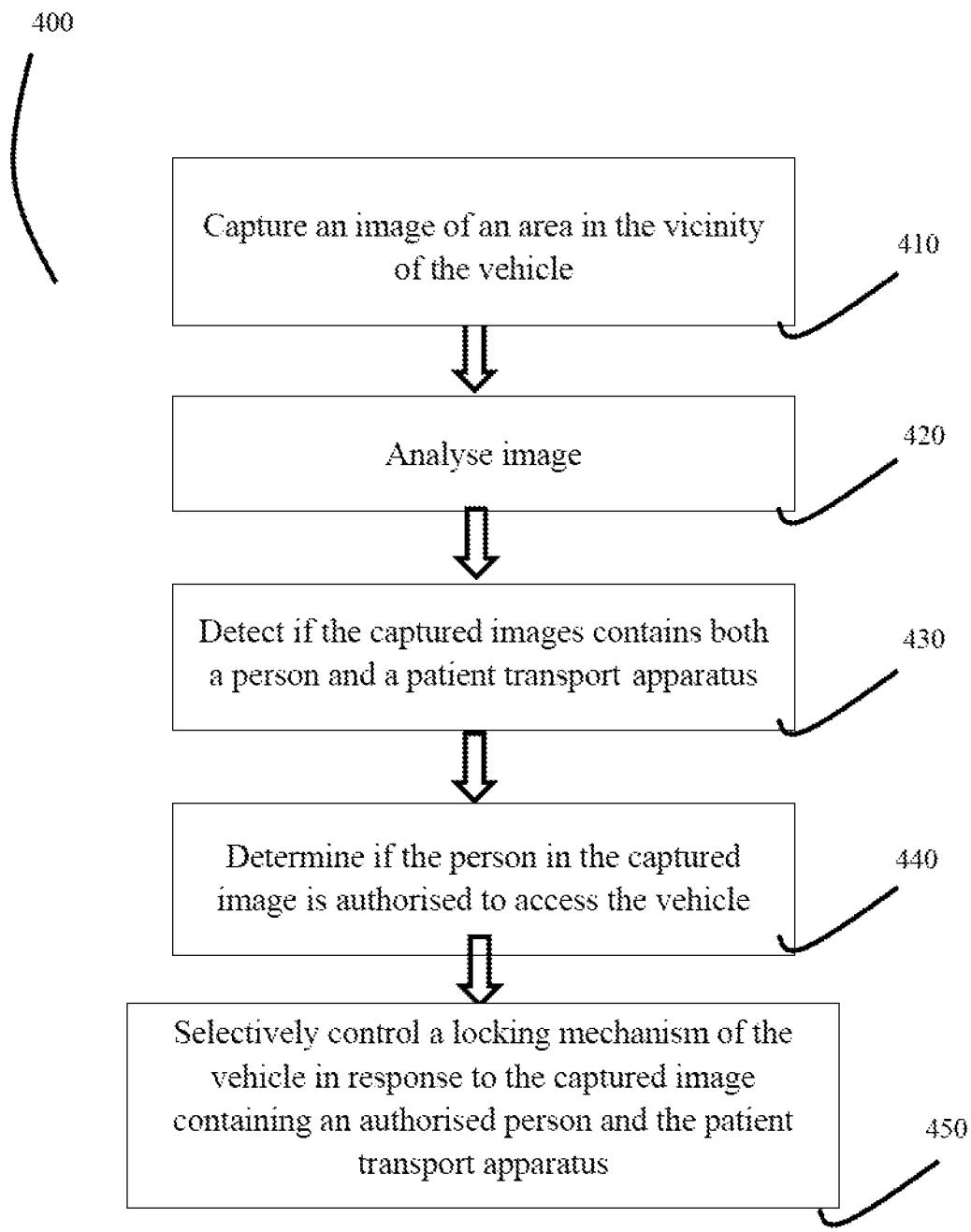
FIG. 4 is an illustration of an exemplary method according to an embodiment of the present disclosure.

Once the image capture device 175 has captured an image of an area in the vicinity of the ambulance 225, the image analysing means 115 may be used to analyse the captured image. The detecting means 120 may then be used to determine if the captured image contains both of the paramedic 205 and the patient transport apparatus 215. If only one or the other, or neither, are detected then the process ends: these steps are best illustrated in FIG. 4 and its associated description.

The processing means 105 may be used to determine if the person—the paramedic 205—is authorised personnel. If the person is determined to be authorised personnel and the patient transport apparatus has additionally been detected to be with them then the locking mechanism 140 on the vehicle (the ambulance 225) may be selectively controlled to be opened by the control means 135. Steps for determining authorisation and access are best illustrated in FIG. 4 and its associated description. In the exemplary embodiment, data relating to authorised personnel including but not limited to biometric markers, as well as data relating to markers for detecting the patient transport apparatus 215, is stored on a database 130 in local memory 110. In an alternative embodiment, data relating to authorised personnel and patient transport apparatus detection is stored on a remote database and is accessed either by the communication means 155 (wirelessly) or by installation at a port before driving to the scene of an incident if it is an ambulance.

In the exemplary embodiment, the processing means 105 is configured to implement machine learning algorithms. It will be understood that this may entail any number of machine learning algorithms including supervised and unsupervised machine learning algorithms as appropriate, for detecting facial and/or other bodily features. For example in one embodiment an unsupervised machine learning algorithm may entail the processing means 105 working in conjunction with the detecting means 120 to group biometric markers from the captured image. The processing means 105 would then seek to match this biometric marker grouping data with biometric data of authorised personnel stored on memory, to authorise a person(s) in the vicinity of the vehicle. In one embodiment, machine learning algorithms may be further used to constantly update and optimise biometric markers associated with personnel as their markers vary naturally over time, so as to avoid possible failed authorisation events. A redundant means (not shown) of overriding the system and/or providing driver credentials may be made available in case of environment setup issues. In one embodiment, a keypad may be placed on the exterior of the ambulance 225 which is operationally associated with the locks on the ambulance 225. Authorised personnel privy to the password may enter the password in to the keypad to unlock the ambulance 225 doors. In a further embodiment, the keypad may additionally or alternatively comprise a finger-print recognition means. In such an embodiment the processing means 105 may be configured to compare biometric data from memory 110 to that provided at the keypad during an access request incident, and process a true/false determination based on a biometric match/failure to authenticate respectively. The processing means 105 would then send the binary determination to the control means 135 which may unlock the ambulance 225 doors if appropriate. In an alternative embodiment, the keypad may comprise a means for processing a proximity card access request or a magnetic stripe card access request.

Referring again to the image analysing means 115, in one embodiment the image analysing means 115 may further be configured to determine if one or both of the authorised personnel and the person on the patient transport apparatus 215 are correctly harnessed according to a predefined protocol. The image analysing means 115 may additionally be configured to determine if a person on the patient transport apparatus 215 is correctly positioned according to a predefined protocol. The predefined protocol may, for example, define that the paramedic 205 may be unharnessed to carry out treatment, but that the patient on the patient transport apparatus 215 must be harnessed correctly with the belt secured over their body and not underneath them. If the patient transport apparatus 215 is a dolly, the predefined protocol may include a requirement that the patient be positioned in an erect position and not slouching: this may further be associated with harnessing requirements, which may help in achieving the positioning end. In the exemplary embodiment, predefined protocols may be stored in a database 130 on local memory 110. Alternatively the predefined protocols may be stored on a remote database and accessed either by the communication means 155 for communicating with the server or by installation at a port before driving to the scene of an incident if it is an ambulance. Ultimately this would assist in the paramedics job in ensuring patient safety and security. The communication means 155 may be wireless, which in one embodiment may be a transceiver.

In one embodiment the control means 135 is configured for controlling operations of a mechanical apparatus associated with the vehicle, such as a vehicle ramp or vehicle lift or the like. In the exemplary embodiment the detecting means 120 is capable of determining the type of patient transport apparatus 215, so as to facilitate the correct instructions being provided to the control means 135 whether a vehicle ramp or lift ought to be actuated in to operation. The detecting means 120 may be configured to determine if the patient transport apparatus 215 is a stretcher, a wheelchair or a dolly to this end. Moreover, the detecting means 120 may be further configured to determine the type of the stretcher the type of the wheelchair or the type of the dolly to this end, since not all patient transport apparatuses require electromechanically assisted access to the ambulance 225. Determining whether or not electro-mechanical assistance is required in this manner not only improves the speed and efficiency of the patient loading process, but also conserves vehicle battery energy. For example, energy would be wasted if the type of stretcher/wheelchair/dolly was not determined and the lift/ramp was lowered/extended unnecessarily and then needed to be returned again. In the exemplary embodiment, the detecting means 120 may further be configured to determine the distance of persons and objects from the vehicle, their duration of time from the vehicle, and the direction and speed of their motion with respect to the vehicle (i.e. moving towards or away from the vehicle and at a certain speed). In such a configuration, protocols for unlocking based on these determinations may be stored in local memory 110.

In the exemplary embodiment the apparatus may additionally comprise the environment measurement means 185 for measuring one or more vehicle environment parameters. The one or more vehicle environment parameters may include but are not limited to vehicle temperature, pressure and humidity. In the exemplary embodiment, the environment measurement means 185 may comprise one or more transducers.

In the exemplary embodiment the apparatus may additionally comprises the external environment measurement means 190 for measuring one or more external environment parameters. The one or more external environment parameters may include but are not limited to ambient temperature, pressure, humidity, wind speed and wind chill. The external environment measurement means 190 may comprise one or more transducers. The external environment measurement means 190 is illustrated as being positioned on the roof of the ambulance 225, however it will be understood that any number of alternative positions are envisaged as being possible such as but not limited to the exterior sidewalls of the ambulance 225.

In the exemplary embodiment, the apparatus further comprises an environment control means 180 for controlling one or more of the vehicle environment parameters. In one embodiment the environment controlling means comprises a heating, ventilation, and air conditioning (HVAC) system. Environment control protocols defining instructions for controlling the vehicle environment parameters may be stored on local memory or communicated wirelessly to the vehicle. In one embodiment, the environment control protocols may be based on various scenarios of external environment parameters. For example, there may be an environment control protocol tailored for when the external environment is 50 degrees Celsius with 80% humidity, and another for when the external environment is -40 degrees Celsius with 80% humidity. Controlling the vehicle environment parameters in this way may be useful if the vehicle environment is at least partially lost to the external environment due to a prolonged period in which the vehicle doors are open during loading. In such an embodiment, the processing means 105 may access the measured external environment parameters from memory, and match them with the closest defined parameter set in memory (e.g. a measured external environment parameter set defined by 47 degrees Celsius and 84% humidity would be matched to a predefined set defined by 50 degrees Celsius with 80% humidity). The processing means 105 may then send from memory the environment control protocol associated with that predefined parameter set to the environment controlling means, which would then regulate the vehicle environment parameters according to that protocol. In another embodiment, the environment protocols based on the measured external environment parameters may further comprise protocols in which the vehicle environment is gradually returned to predefined optimal conditions with respect to the external environment parameters. This may be useful, for example, when treating a patient with severe heatstroke: it is commonly advised to not introduce one suffering from severe heatstroke to a very cool environment immediately from a very hot environment as this can have an adverse affect on their health.

In a further embodiment, the control means 135 may be configured to conserve vehicle battery power by dynamically adjusting the power output of the environment control means 180, in dependence on one or a combination of one or more vehicle environment parameters, one or more external environment parameters, the duration the vehicle doors have been open and the duration of the presence of authorised personnel in the vicinity of the vehicle.

In the exemplary embodiment the apparatus may additionally comprise a recording means 125 for writing to memory protocol adherence history. In the exemplary embodiment, the communication means may be used to transmit data relating to protocol adherence by authorised personnel from local memory to a remote database. A user profile of each of the authorised personnel containing their protocol adherence history may be formed on a remote database. Tracking protocol adherence of any member of ambulance crew may be useful for investigative purposes ex post facto, or for staff training purposes among other uses. In an alternative embodiment, an event of protocol violation may be transmitted in real-time to a remote server via the communication means 155. Real-time updates such as this may be implemented for example in conjunction with a control centre which can communicate with ambulance staff and/or control vehicle parameters such as but not limited to maximum speed and acceleration. Step 340 of FIG. 3 best illustrates the aspect of the embodiment including the control centre.

The recording means 125 may further be configured to synchronously write to memory patient status data (such as heartrate, blood pressure etc.), vehicle environment data such as temperature and vehicle parameter data such as speed and acceleration. Synchronously recording such data may be useful for investigative purposes ex post facto, or for staff training purposes among other uses. The synchronously recorded data may further include time stamps. The harnessing and positioning protocol adherence data may further be associated with the synchronously recorded data via time stamps.

In one embodiment, the detecting means 120 may be further configured for detecting fluid spillage. The fluid may include but is not limited to blood or vomit. In such an embodiment, the recording means may further be configured to write fluid spillage incidents to memory. Fluid spillage incidents may be further associated with the synchronously recorded data via time stamps. In the exemplary embodiment, data regarding markers for identifying different types of fluids may be stored on local memory 110. Alternatively the data regarding markers for identifying different types of fluids may be stored on a remote database and accessed either by the communication means 155 for communicating with the server or by installation at a port before driving to the scene of an incident if it is an ambulance. The communication means 155 may be a wireless communication means 155.

In the exemplary embodiment, the processing means 105 may further be configured to compile a report containing one or more of the synchronously recorded data, harnessing protocol adherence, positioning protocol adherence and fluid spillage, to be transmitted wirelessly to a remote server or remote database. Alternatively, the processing means 105 may compile the report and write it local memory for retroactive review.

In one embodiment, the control means 135 may be operationally associated with the vehicle electromechanical actuators 150 on-board the vehicle to perform one or more of the tasks outlined above including but not limited to vehicle environment parameter control, selective locking of vehicle doors and ramp or lift actuation.

FIG. 2 further illustrates a plan view of the interior volume 235 of the rear of the ambulance 225 according to an embodiment of the present disclosure, which contains a plurality of the image capture device 175 mounted on its sidewalls. The image capture device 175 may alternatively be mounted on the ceiling of the interior of the ambulance 225. Having the image capture device 175 installed in the interior of ambulance 225 may serve the purpose of capturing images for the detection of fluid spillage and for determining if harnessing and patient positioning protocols are abided by at all times. In terms of determining harnessing and positioning protocols, the use of image analysis to determine adherence removes the need for an integrally installed seat with one or both of harnesses integrally connected to the vehicle electromechanical actuators 150 and pressure sensors under the seats/patient transport apparatus 215 integrally connected to the vehicle electromechanical actuators 150. In this respect, a "dumb" patient transport apparatus 215 (that is, one not being integrally connected or connectable to the vehicle) can be used, providing greater flexibility of choice whilst still being able to provide protocol adherence monitoring at all times. In the exemplary embodiment, machine learning algorithms may be implemented to detect if authorised person(s) and the patient are harnessed correctly and if the patient is positioned correctly. Harnesses 240 may be of any colour and consist of any pattern. Machine learning algorithms may include deep learning algorithms implementing neural networks. In a further embodiment, one or more of edge detection, object recognition, pattern matching, gauging or metrology (object size and distance measurement) and image matching may be implemented together with, or as an alternative to, machine learning algorithms. These techniques may be implemented once on any single frame or dynamically on a live feed comprising a plurality of frames.

Figure 3:
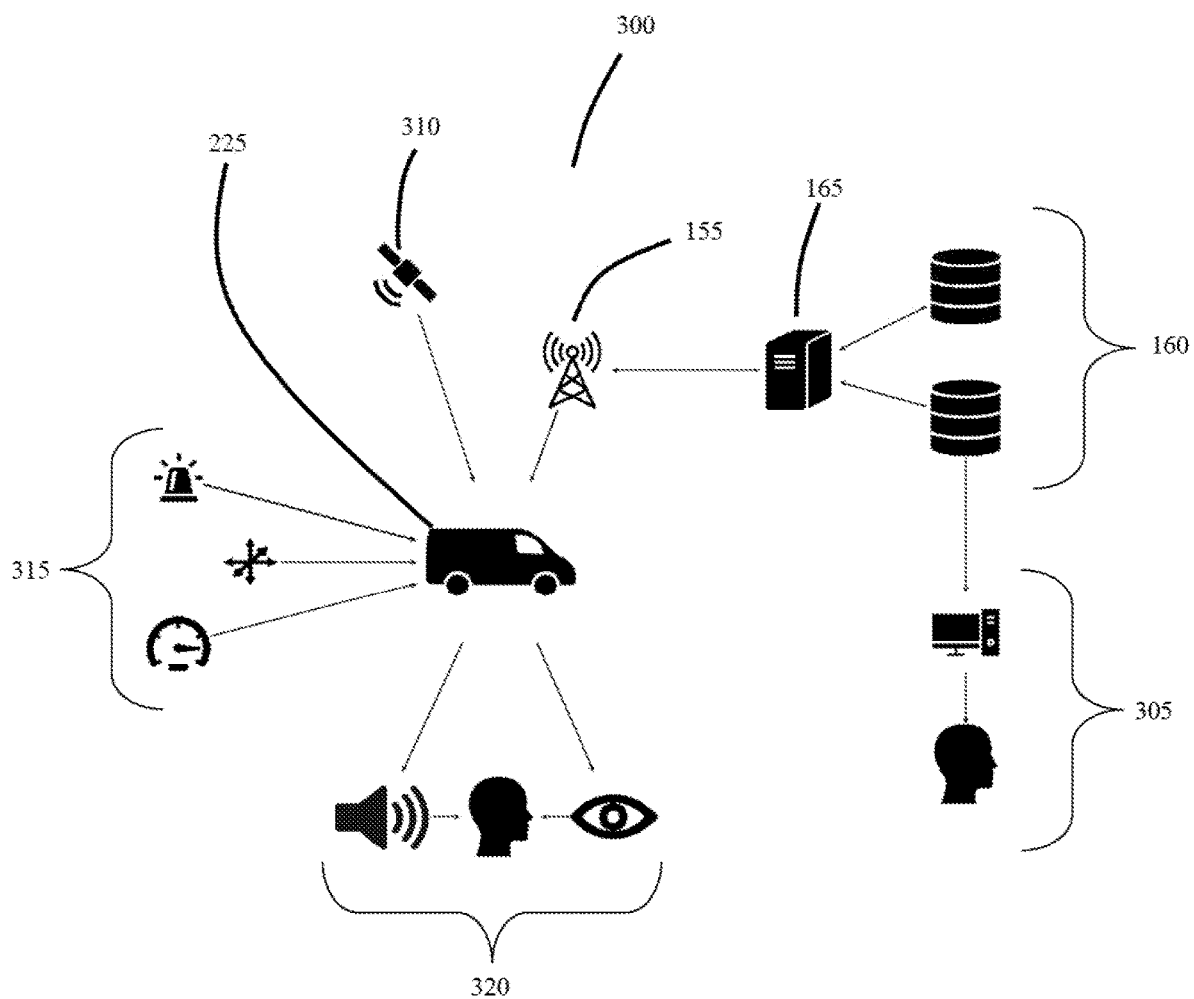
FIG. 3 is an illustration of a system according to an embodiment of the present disclosure.
Figure 20:
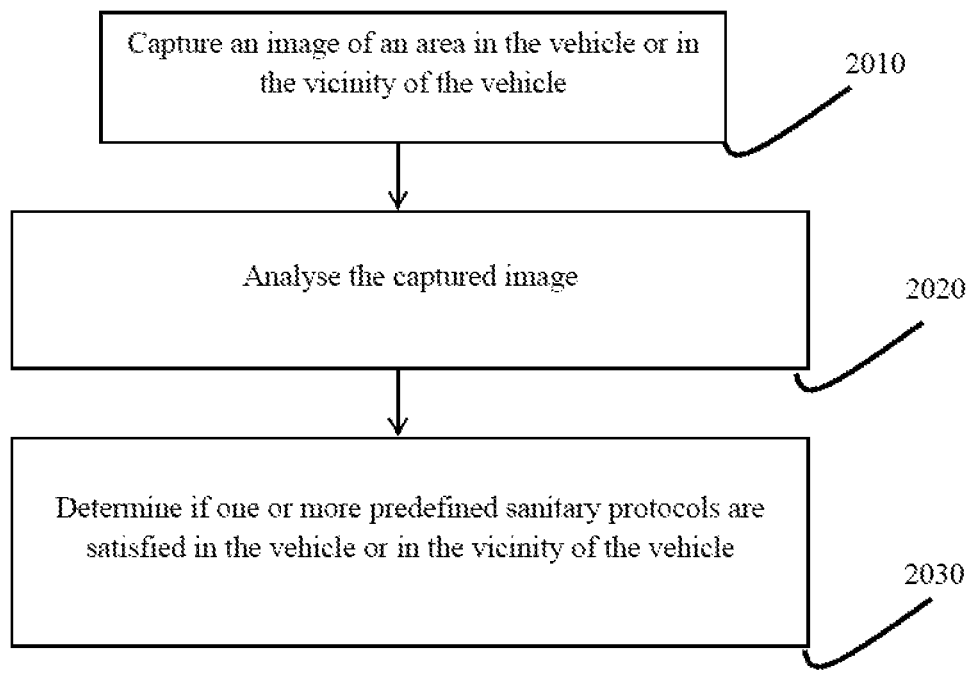
FIG. 20 is an illustration of an exemplary method according to an embodiment of the present disclosure.
Figure 21:
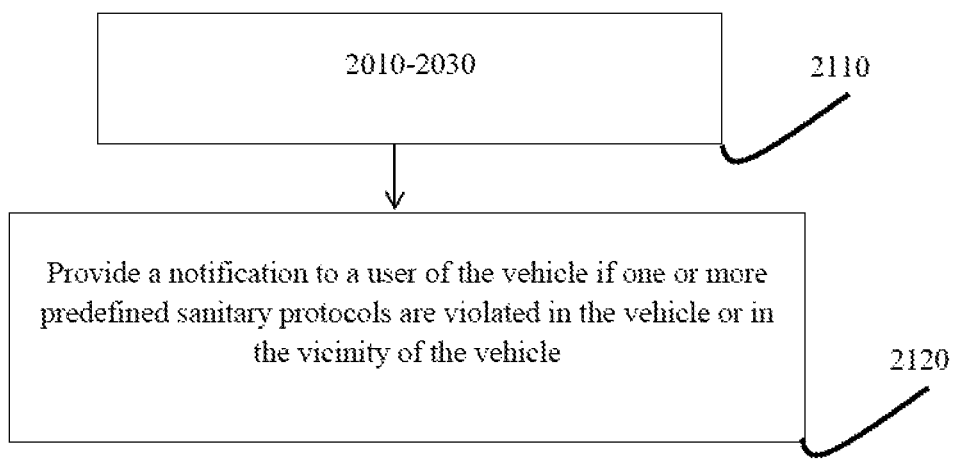
FIG. 21 is an illustration of an exemplary method according to an embodiment of the present disclosure.
Figure 22:
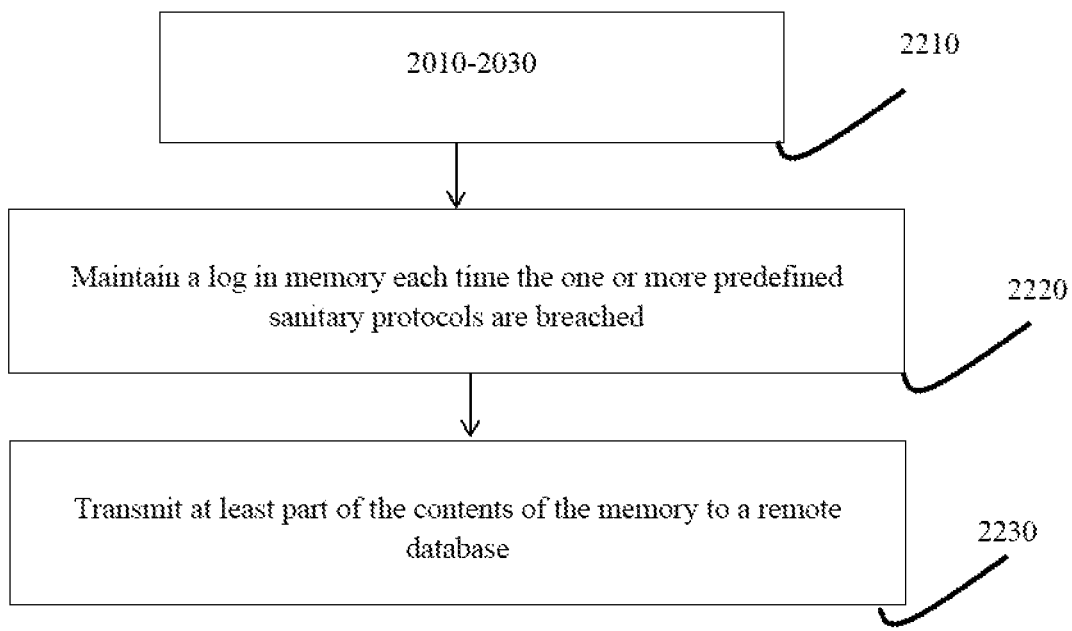
FIG. 22 is an illustration of an exemplary method according to an embodiment of the present disclosure.

FIG. 3 is an illustration of a system 300 according to an embodiment of the present disclosure. The system 300 comprises the ambulance 225 fitted with a wireless communication means 155 capable of communicating with the remote server 165, itself capable of transmitting and receiving information to and from remote database(s) 160. The remote database(s) 160 may be further associated with a remotely located control centre 305 capable of receiving, processing and transmitting information back downstream to the ambulance 225 via the remote server 165. The wireless communication means 155 may transmit information such as geographical position, based on the communication of the ambulance 225 with a geographical positioning satellite system 310. The wireless communication means 155 may also transmit vehicle parameter data from various on-board facilities 315 such as but not limited to a gyroscope, a speedometer and an emergency lights status clock. Furthermore, the wireless communication means 155 may transmit the data outlined above including but not limited to synchronously recorded data, harnessing protocol adherence, positioning protocol adherence and fluid spillage. The report containing this data—compiled by the processing means 105—may be transmitted to the remote server 165 and stored on the remote database(s) 160. The report may be compiled in real-time or ex post facto. If the report is compiled in real-time, the report may further be transmitted in real-time to the control centre 305 for real-time review. In one embodiment, when a fluid spillage event is detected the vehicle 225 is automatically removed from a real-time dossier of fleet vehicles available for use, and the control centre 305 is alerted that the vehicle 225 is contaminated. Only once the vehicle 225 has been decontaminated according to territorially defined medical hygiene standards and this fact recorded with the control centre 305, will the vehicle 225 reappear in the real-time dossier and be made available for use. The control centre 305 may be able to selectively change and/or reduce the personnel who may be authorised to access a quarantined vehicle. More generally, the control centre 305 may determine who is authorised to access the vehicle 225 at any one time. FIGS. 20-22 provide further exemplary methods of safety control in a vehicle, consistent with embodiments of the present disclosure. As discussed above, having the image capture device 175 installed in the interior of ambulance 225 may serve the purpose of capturing images for the detection of fluid spillage. However, it will be understood that contamination and sanitary protocol violation events are not constrained to the interior volume of a vehicle. Indeed, any of blood spillage, the presence of vomit or other potentially contagious body fluids, improper waste disposal, the presence needles or other exposed sharp objects may be present external to the interior volume of the vehicle. Accordingly, it is envisaged in the above that the detecting means may be configured for detection of sanitary protocol violation events in the interior volume of the vehicle but also feasibly in the area surrounding the vehicle. What is more, sanitary protocol violation events may also comprise one or more of the absence of personnel protective equipment (gloves, sanitary garments such as but not limited to gowns, respirators, safety masks, protective eyewear and the like) and unsafe injection practices by (e.g.) authorised vehicle personnel or by others. Sanitary protocol violation events may comprise unsafe exposure or presence of hazardous objects such as but not limited to: a syringe, a knife, or a fragment of a resilient material, where the resilient material may comprise (e.g.) one or more of a glass, a metal, a wood. Accordingly, the detecting means may be configured to detect any of the above sanitary protocol violation and events, and the processing means may record them in a log in memory. Moreover, it will be understood that the detection of fluid spillage in and around the vehicle is not necessarily contingent on authorised personnel being present in or around the vehicle. However, as discussed previously, if a log of predefined safety protocol violation is maintained, in some embodiments it may be advantageous to detect an authorised person(s) and associate protocol violation events to their unique ID. Accordingly, this may form part of a report compiled by the processing means. In alternative embodiments, 'sanitary' may be generalised to 'safety', i.e. safety protocols, since the present invention is not constrained to use in medical applications. In such embodiments, safety protocol violation may comprise the absence of certain law-enforcement/security equipment and the like.

A series of user notification modules 320 for providing notifications to a user of the vehicle may be actuated by a number of processes via the control means 135. The user notification modules may include a visual notification means such as an LCD display capable of producing visual messages, or an audio system capable of producing audio messages. In one embodiment, the control centre 305 may be monitoring vehicle parameter data in real-time and may communicate notifications to be relayed to personnel on-board the ambulance 225 via one or more of the user notification modules 320. In another embodiment, when harnessing and/or patient positioning protocols are detected as being breached one or more of the user notification modules 320 may provide a notification to personnel on-board the ambulance 225. Protocol breach notifications may be stored in local memory to be accessed by the processing means 105 and routed to the control means 135 which may actuate one or more of the user notification modules 320).

In various embodiments of the present disclosure, the image analysing means 115 may be configured to count a number of persons in the vicinity of the vehicle at any given time. Counting a number of persons present in the interior or the exterior of the vehicle may furthermore comprise detecting the category of the persons and counting each. For example counting a number of authorised personnel, a number of patients, and so on. Authorised personnel may be detected by unique ID badges or codes disposed on their outerwear, via facial recognition and/or detection of a uniform based on certain characteristics such as colours or markers. Using machine learning algorithms or otherwise, the imaging analysis means 115 may also be configured to detect when a person has entered or exited the interior of the vehicle and associate a time stamp with said event. For example, this may be used to determine whether a vehicle has been used and so if there is a need to flag the vehicle for cleaning. Detecting the number of persons present within the vehicle may be used control the interior lighting of the vehicle as well as any interior environment control systems, to produce the most optimal and desirable environmental conditions within the vehicle.

FIG. 4 is an illustration of an exemplary method 400 according to an embodiment of the present disclosure. Initially, an image of an area in the vicinity of the vehicle is captured, step 410. The image is then analysed, step 420. The image is analysed to detect if the captured image contains both a person and a patient transport apparatus, step 430. The image is further analysed to determine if the person in the captured image is authorised to access the vehicle. The locking mechanism 140 of the vehicle is selectively controlled in response to the captured image containing an authorised person and the patient transport apparatus, step 450. The first step 410 may be carried out at all times, or only when the vehicle engine is running. Alluded to in the description of FIG. 2 was the third step 430, wherein the detecting means 120 determines if the image captured by the image capture device 175 contains both a person and a patient transport apparatus 215. If only one or the other, or neither, are detected then the process ends and returns to 410. If both are detected then the process proceeds to 440 where the processing means 105 is used to determine, based on data from a biometric database of all ambulance staff, if the person is authorised personnel, i.e. the paramedic 205. If the person is authorised then the process proceeds to 450 wherein the control means 135 selectively unlocks one or more doors of the ambulance 225. Both the cab doors and rear doors, or one or the other, may be opened: this may be predefined with a set of instructions stored in memory. The step 430 may further comprise determining that the person and patient transport apparatus are detected to be one or a combination of: within a predefined required distance from the vehicle: a predefined required duration of time within the vicinity of the vehicle; and detected to be moving towards the vehicle. In one embodiment, the predefined required distance may be 10 metres. In another embodiment, the predefined required duration of time within the vicinity of the vehicle may be 10 seconds. In a further embodiment, the step 430 may combine the duration of time the person and patient transport apparatus are within the vicinity of the vehicle with the detection of them moving towards the vicinity of the vehicle, so as to reduce the occurrence of false positives.

Figure 5:
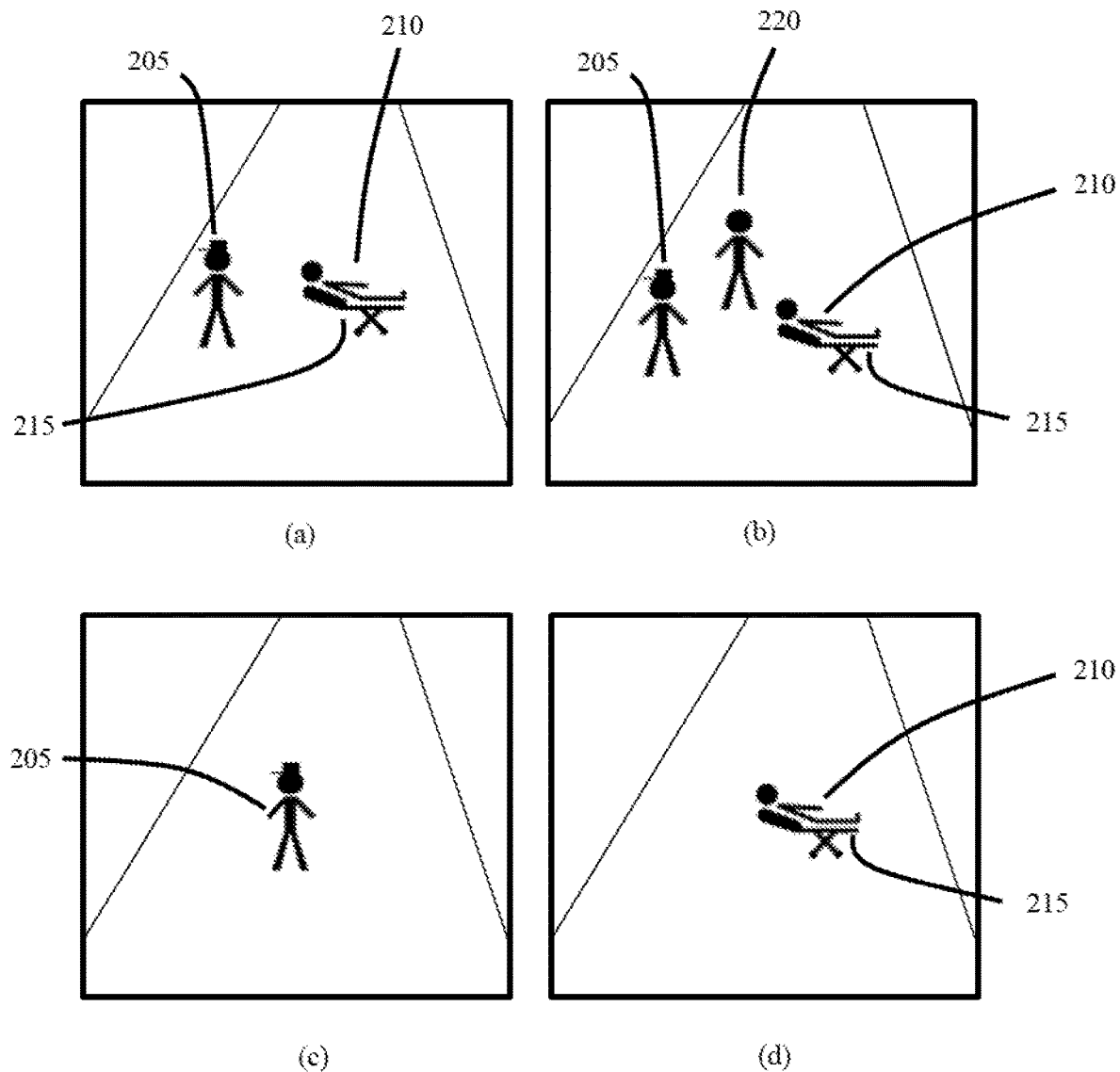
FIG. 5 is an illustration of a plurality of scenarios according to an embodiment of the present disclosure.

FIG. 5 is an illustration of possible scenarios the image capture device 175 may capture. Referring to FIG. 5*a*, there is illustrated an embodiment in which both an authorised person 205 and a patient transport apparatus 215 are within the area captured by the image capture device 175. According to the method illustrated in FIG. 4, detection of a person and a patient transport apparatus 215 followed by authorisation of said person, is followed by selectively controlling the locking mechanism 140 of the vehicle in response to the captured image containing an authorised person and the patient transport apparatus, step 450. In further embodiments illustrated in subsequent Figures this may be followed by additional method steps.

Referring to FIG. 5*b*, there is illustrated an embodiment in which an authorised person 205, a patient transport apparatus 215 and a further person 220 are within the area captured by the image capture device 175. In the exemplary embodiment, if the further person 220 is detected as being in the captured image then access to the vehicle may be denied. In an alternative embodiment, the detecting means 120 may be configured to detect if the motion of the further person 220 matches a predefined "violent behaviour profile"; such a profile may be stored on local memory 110. The predefined "violent behaviour profile" may comprise one or more of select facial expressions, arm movements or other bodily movements which are predefined as being typical of a person who presents a threat of violence. If the further person 220 is determined by the detecting means 120 as matching such a profile then access may be denied. The purpose of the "violent behaviour profile" might be to avoid instances wherein the paramedic 205 and patient transport apparatus 215 are denied access to the ambulance 225 because of the presence of a further person 220 who poses no threat. In a further embodiment, alternative access authorisation methods may be implemented for such an instance as in 5*b*. For example, the control centre 305 may be able to commandeer the image capture device 175 in real-time, assess the situation apparent from the image captured and make an authorisation decision on that basis.

Referring to FIG. 5*c*, there is illustrated an embodiment in which an authorised person 205 is within the area captured by the image capture device 175, but not a patient transport apparatus 215. In the absence of a patient transport apparatus 215, the authorised person 205 may be denied access to the vehicle, according to the method of FIG. 4. In one embodiment, alternative access authorisation methods may be implemented for such an instance as in 5*c*. For example, the authorised person 205 may be able to contact the control centre 305: the control centre 305 may then be able to commandeer the image capture device 175 in real-time, assess the situation apparent from the image captured and make an authorisation decision on that basis.

Referring to FIG. 5d, there is illustrated an embodiment in which a patient transport apparatus 215 is within the area captured by the image capture device 175, but not a person. In the absence of a person, subsequent steps beyond detecting if the captured image contains both a person and a patient transport apparatus 215 may be aborted. In one embodiment, the control centre 305 may be able to commandeer the image capture device 175 in real-time, assess the situation apparent from the image captured and make decisions on that basis including but not limited to contacting personal radios of authorised person 205.

Figure 6:
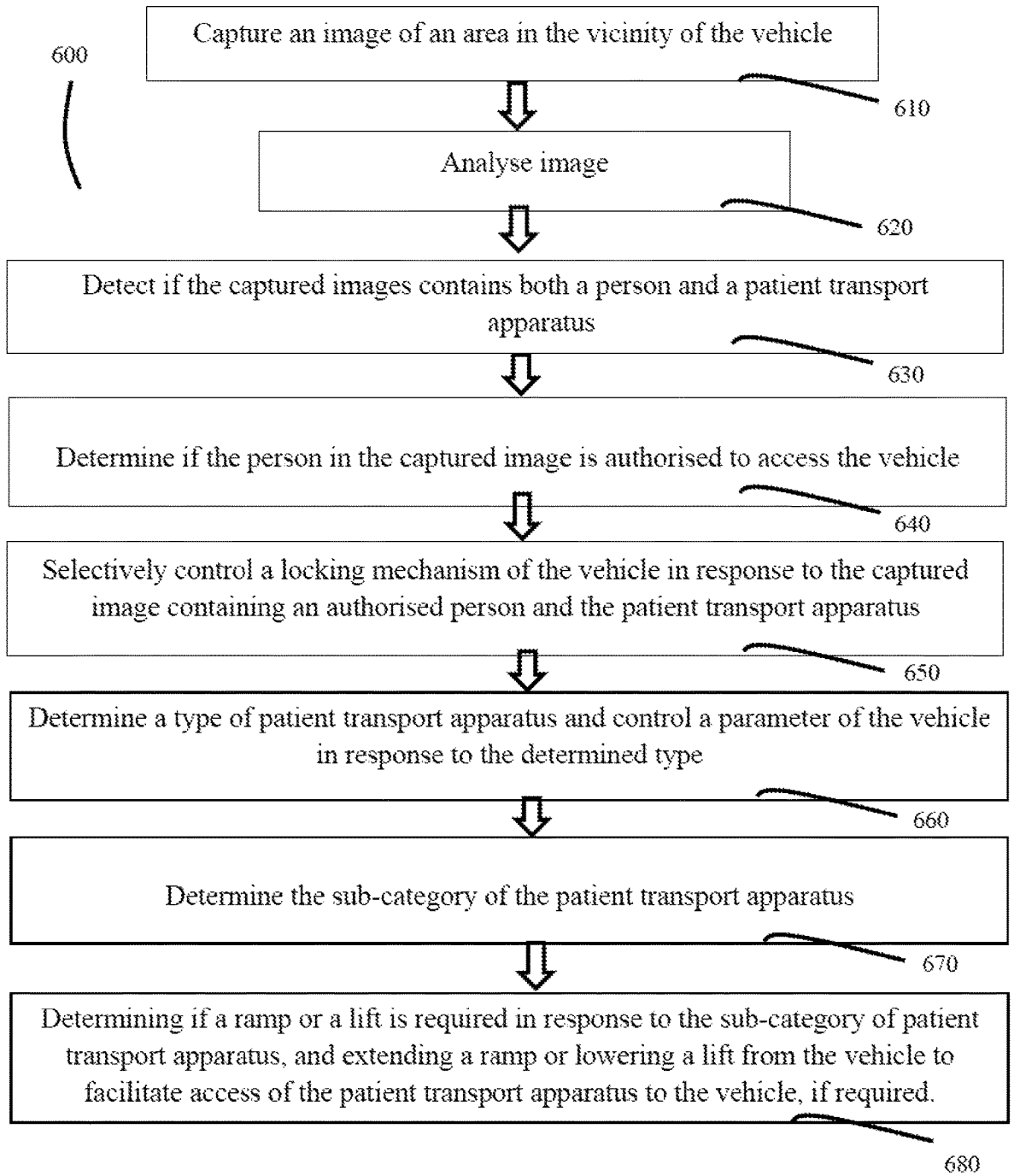
FIG. 6 is an illustration of an exemplary method according to an embodiment of the present disclosure.

FIG. 6 is identical to the method of FIG. 4, but with the addition of steps 660-680 relating to facilitating access to the vehicle on the basis of the type of patient transport apparatus in use. Once it has been determined that there is both an authorised person 205 and a patient transport apparatus 215 in the captured image 630-640, and the vehicle doors have been selectively unlocked, step 650, the detecting means 120 determines the type of patient transport apparatus 215, step 660. The sub-category of the patient transport apparatus is then determined, step 670. The type of patient transport apparatus 215 may be a stretcher, a wheelchair or a dolly: the sub-category may be the type of the stretcher, the type of the wheelchair or the type of the dolly. A ramp is then extended or a lift lowered from the vehicle in response to the sub-category of patient transport apparatus 215 if it is determined to be necessary, step 680. The 'if required' clause is important in light of the fact that not all patient transport apparatuses require electro-mechanical assistance to access the ambulance 225. As outlined above in relation to FIG. 2, determining if any one of the ramp or lift is required can save time and energy in the instances where they are not required. Data relating to markers for identifying the various patient transport apparatuses, as well as data relating to ramp/lift protocols based on the type of patient transport apparatus, may be stored on local memory. In various exemplary embodiments, one or more of the steps of FIG. 6 may be omitted. For example, in one embodiment the method may comprise: 610-660 only. For example, in another embodiment the method may comprise: 610-660 followed by 680 only. For example, in another embodiment the method may comprise: 610-670 only. For example, in another embodiment the method may comprise: 610-660 followed by providing a notification to a user of the vehicle which means of access to the vehicle is substantially suitable based on the type of patient transport apparatus determined in step 660. In various embodiments, such a notification may be audio and/or visual. In further embodiments, a predefined list of authorised transport apparatus types may be stored in memory (locally or remotely), and as such in various embodiments where the type and possibly sub-type of transport apparatus is determined, the processing means may be further configured to determine if the type of patient transport apparatus is an authorised type of patient transport apparatus. Moreover, as discussed above the term 'patient transport apparatus' may be replaced by 'personnel transport apparatus', since the present invention is not limited to ambulances or other medical care vehicles. Furthermore, in some embodiments the detection and authorisation of personnel may be omitted-such embodiments are best presented in FIGS. 11-14.

Figure 7:
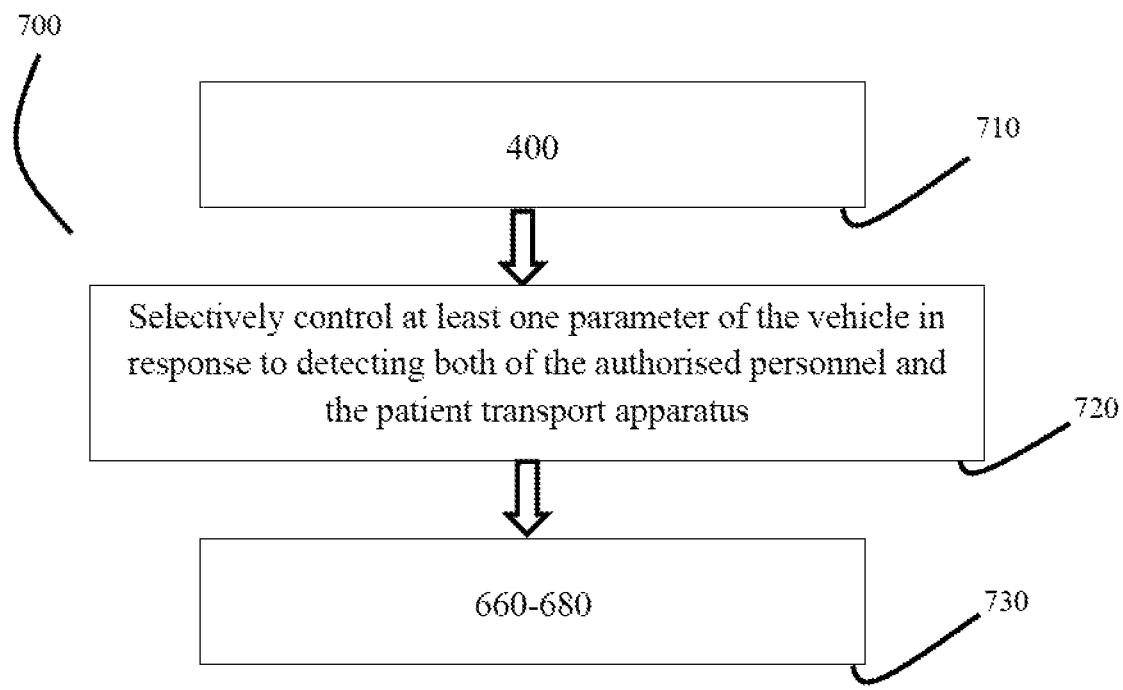
FIG. 7 is an illustration of an exemplary method according to an embodiment of the present disclosure.

FIG. 7 is an illustration of an exemplary method 700 according to an embodiment of the present disclosure, containing the steps of the embodiment of FIG. 4 (710) followed by the step of selectively controlling at least one parameter of the vehicle in response to detecting both the authorised personnel and patient transport apparatus approaching the vicinity of the vehicle, step 720. Subsequent to step 720 are steps 660-680 of FIG. 6 (730). In one embodiment, the vehicle parameter may be a vehicle environment parameter such as temperature, pressure or humidity. For example, in an extreme weather environment where losing the vehicle environment to the external environment may happen in a short time, it may be useful to begin combating loss of the vehicle environment immediately following actuation of the doors to unlock. The environment control means 180 would immediately begin enacting a predefined environment control protocol accessed from memory 110 by the processing means 105. In an alternative embodiment, the vehicle parameter may include but is not limited to vehicle ignition, emergency scene lights and electrically powered medical equipment charging facilities.

Figure 8:
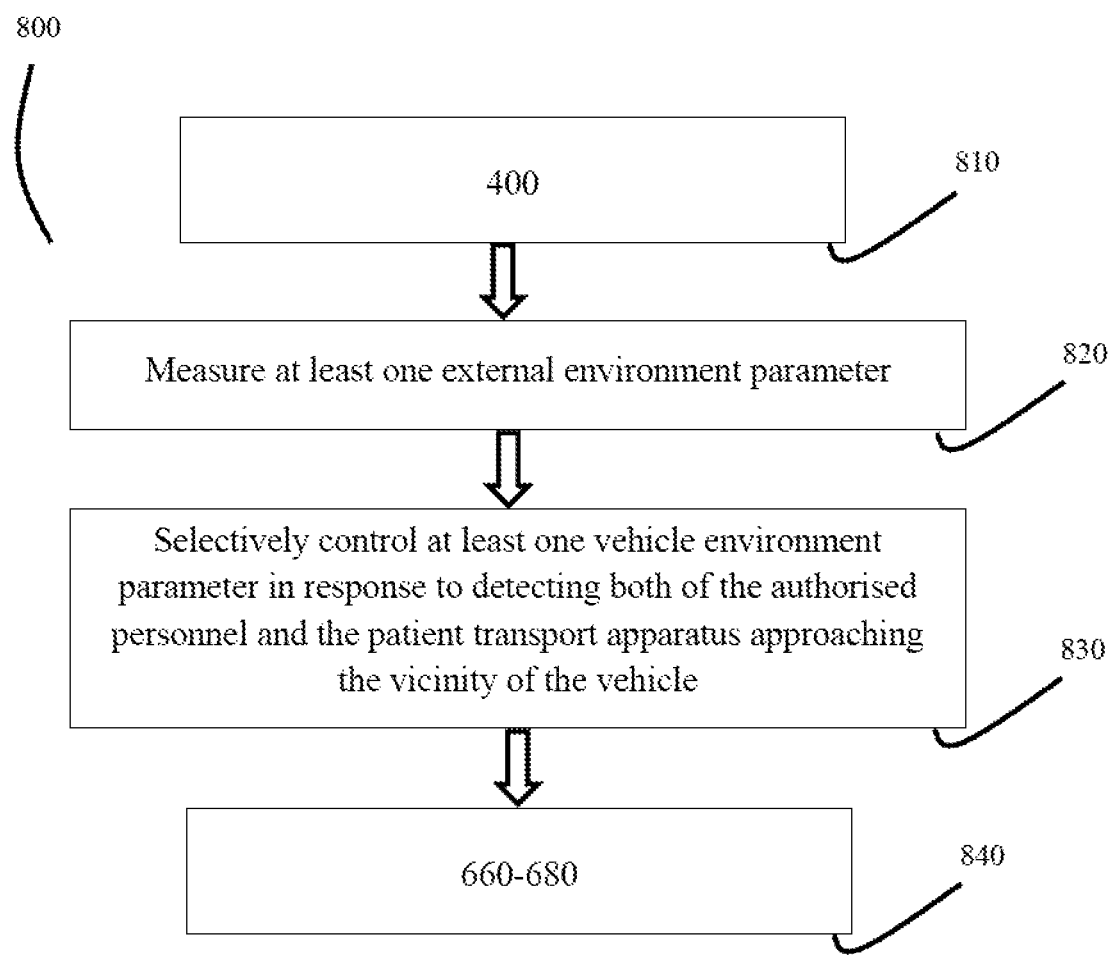
FIG. 8 is an illustration of an exemplary method according to an embodiment of the present disclosure.

FIG. 8 is an illustration of a method 800 involving vehicle environment control but in dependence upon measured external environment parameters. The method 800 contains the steps of the embodiment of FIG. 4 (810). Once a person and patient transport apparatus 215 have been detected, the person has been authorised and the locking mechanism 140 of the vehicle selectively controlled, at least one external environment parameter is measured, step 820. Subsequently, at least one vehicle environment parameter is selectively controlled in response to detecting both the authorised personnel and patient transport apparatus approaching the vicinity of the vehicle, step 830. As described in relation to FIG. 2, the processing means 105 may match the at least one measured external environment parameter to a predefined environment control protocol associated with the closest defined parameter set in memory. The processing means 105 may then communicate this protocol to the environment control means 180, which would subsequently regulate the vehicle environment parameters according to that protocol. Subsequent to step 830 are steps 660-680 of FIG. 6 (840).

Figure 9:
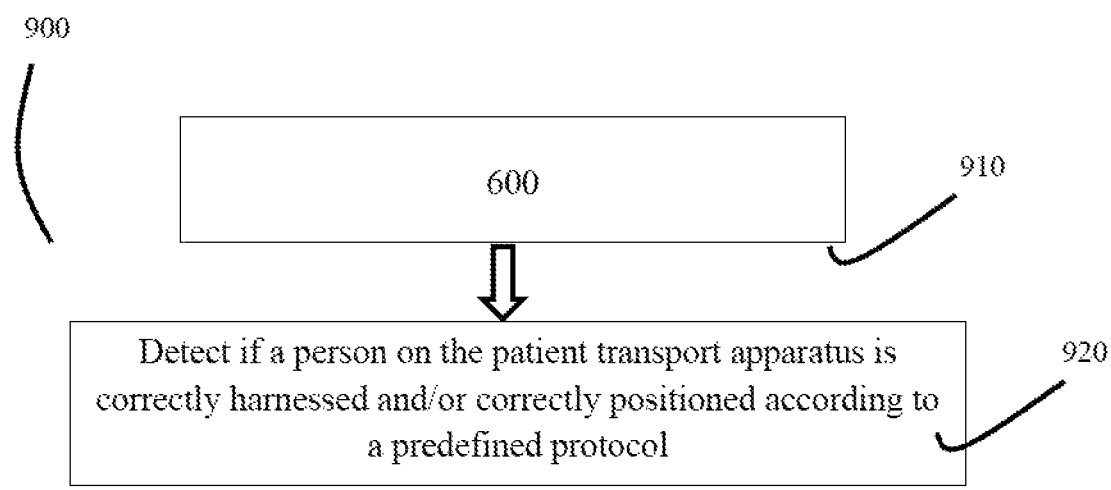
FIG. 9 is an illustration of an exemplary method according to an embodiment of the present disclosure.

FIG. 9 is an illustration of a method 900 according to an embodiment of the present disclosure, identical to the method 600 of FIG. 6, but with the additional step of detecting if patient harnessing and/or patient positioning protocols have been adhered to according to a predefined protocol, step 920.

Figure 10:
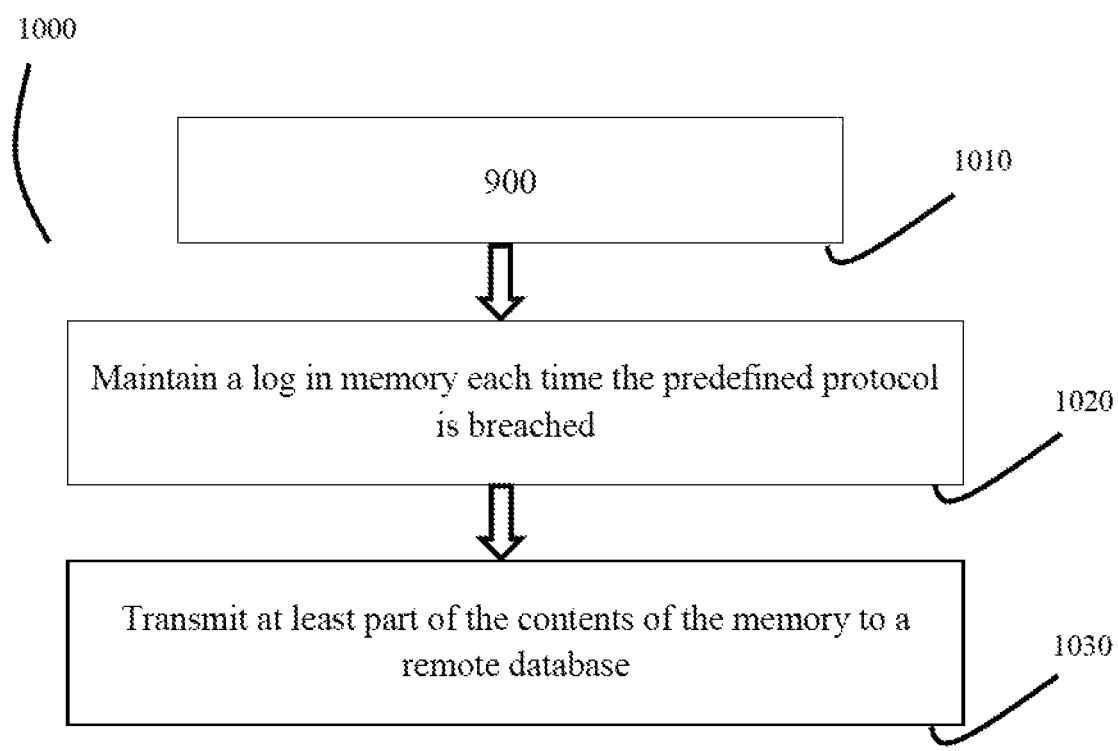
FIG. 10 is an illustration of an exemplary method according to an embodiment of the present disclosure.

FIG. 10 is an illustration of a method 1000 according to an embodiment of the present disclosure, identical to the method 900 of FIG. 9 (1010), but with the additional steps of maintaining a log in memory each time the predefined protocol(s) for harnessing and/or positioning is/are breached, step 1020, and transmitting at least part of the contents of the memory to a remote database(s), step 1030. The at least part of the contents of the memory may be transmitted to the remote database(s) wirelessly via the wireless communication means 155 or via wired means for example once the ambulance 225 has returned to its station after a response incident.

Figure 11:
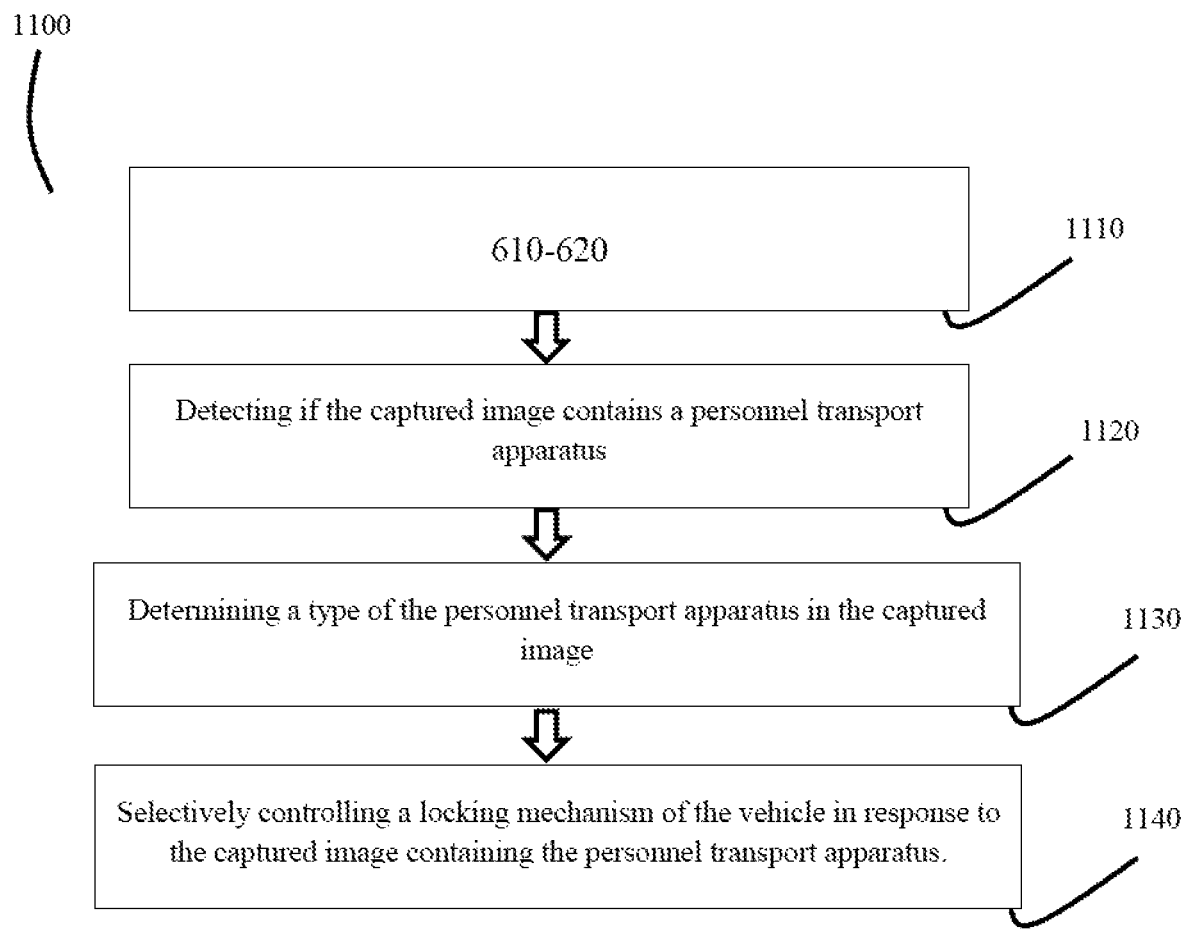
FIG. 11 is an illustration of an exemplary method according to an embodiment of the present disclosure.
Figure 12:
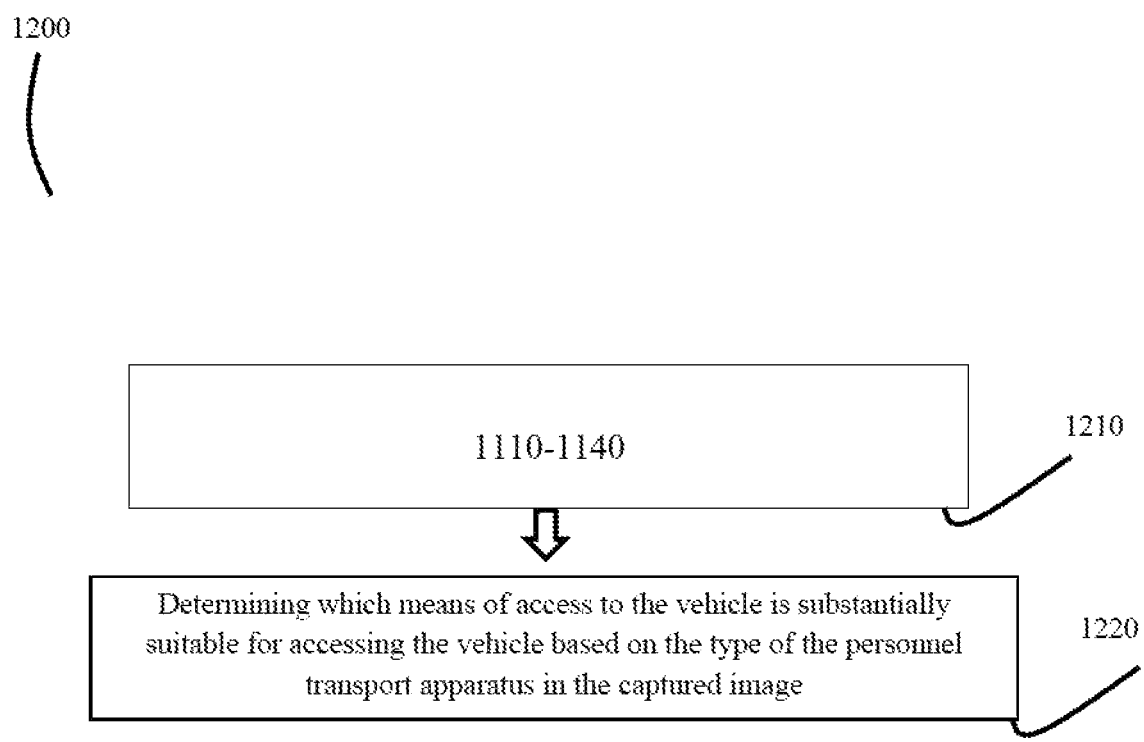
FIG. 12 is an illustration of an exemplary method according to an embodiment of the present disclosure.
Figure 13:
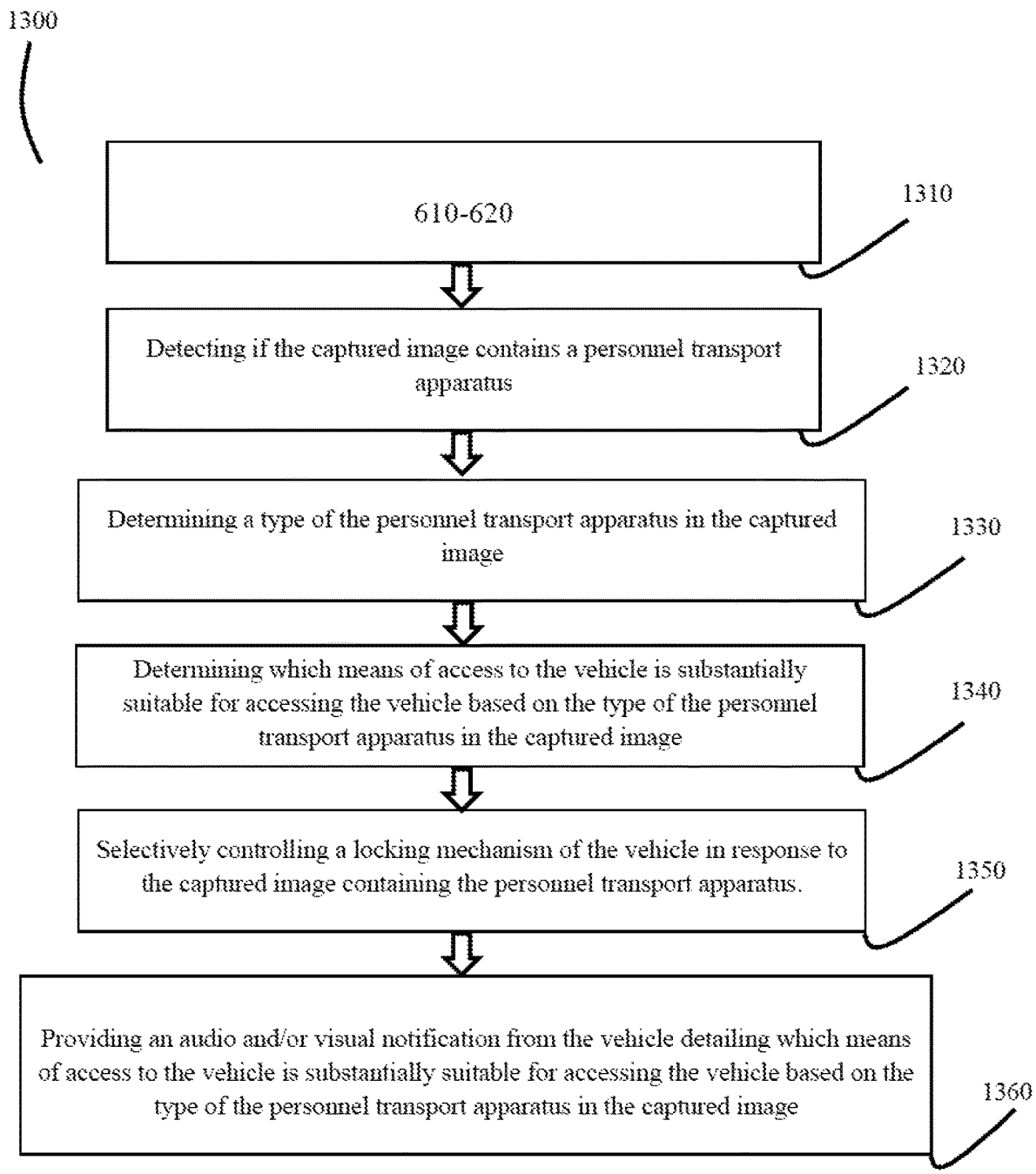
FIG. 13 is an illustration of an exemplary method according to an embodiment of the present disclosure.

Referring to FIG. 11, there is provided a method 1100 of controlling access to a vehicle based on detecting 1120 a patient transport apparatus and further determining 1130 a type of the patient transport apparatus. Subsequently, the method 1100 comprises selectively controlling 1140 a locking mechanism of the vehicle in response to the captured image containing the personnel transport apparatus. FIG. 12 illustrates a further embodiment 1200 where, in addition to the steps 1110-1140 of FIG. 11 (1210), there is provided the additional step of determining 1220 which means of access to the vehicle is substantially suitable for accessing the vehicle based on the type of the personnel transport apparatus in the captured image.

In some embodiments, the vehicle may be equipped with a notification means. The notification means may be configured to provide a notification, such as an audio and/or visual notification, from the vehicle detailing which means of access to the vehicle is substantially suitable for accessing the vehicle based on the type of the patient transport apparatus in the captured image. An example of an embodiment wherein the provision of a notification is included is given in FIG. 13, which illustrates a method 1300 including steps 1310, 1320, 1330, 1340, 1350, 1360. If neither the lift nor the ramp are suitable based on the type of the patient transport apparatus detected, the notification means may provide a notification in such an instance too. Other means of access to the vehicle may include manual access via the door(s) of the vehicle. The notification means may comprise an audible or visual alarm. For example, the notification means may comprise the sirens and/or one or more lights mounted on the vehicle such as the siren lights of an emergency vehicle. In addition or alternatively, a notification may be provided to a remote device of one or more personnel indicating which means of access to the vehicle is suitable. Said remote device may be communicatively coupled to the notification means or another component of the vehicle such as but not limited to the control means or the processing means.

In any of the embodiments of the present disclosure, if a person is not detected as being present on the personnel transport apparatus, the vehicle system may default to manual access (rather than the automatic extension of an access means such as the vehicle lift or ramp) and manual authentication. The processes may terminate or continue to authenticate any personnel in the vicinity of the vehicle, and in such embodiments where the process continues to authentication the process may selectively control 1350 the locking mechanism in response to the captured image containing the personnel transport apparatus and an authenticated person.

Figure 14:
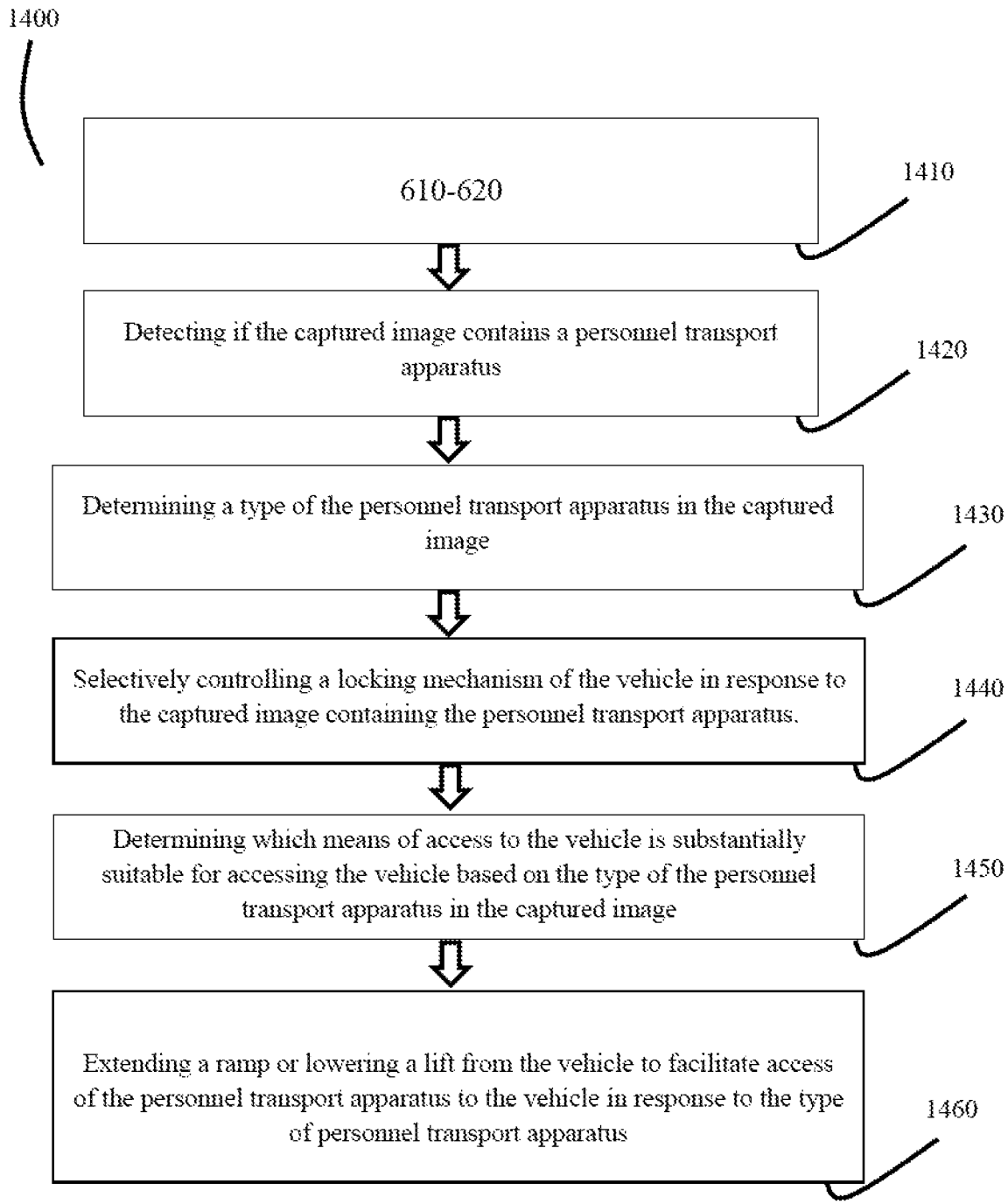
FIG. 14 is an illustration of an exemplary method according to an embodiment of the present disclosure.

Referring to FIG. 14, there is provided a method 1400 similar to that of FIG. 12, (and including steps 1410, 1420, 1430, 1440 and 1450) but including the further step 1460 of extending a ramp or lowering a lift from the vehicle to facilitate access of the patient transport apparatus to the vehicle in response to the type of patient transport apparatus. As discussed, it may alternatively be determined that neither the lift nor the ramp are appropriate in view of the determined type of patient transport apparatus—in such cases, a notification may be provided as in FIG. 12 (however it will be understood that the provision of a notification may also apply to cases where the ramp or lift are indeed determined to be appropriate). In some embodiments, if neither the ramp nor the lift are deemed appropriate, the vehicle system, may default to manual. Alternatively, other means of access to the vehicle may be actuated to open, where available.

As discussed in the foregoing, it may be desirable in some embodiments to determine whether the type of patient transport apparatus in the vicinity of the vehicle is an authorised type of patient transport apparatus. For example, a certain type of wheelchair or dolly may not meet the health and safety requirements associated with the vehicle in question. Authorised personnel may have the option, possibly subject to the provision of a security pass, to override the requirement that the type of the patient transport apparatus is an authorised patient transport apparatus. In some embodiments, such an override event may be included in the report compiled by the processing means 105. As discussed above, data relating to authorised types of patient transport apparatuses may be stored on local memory or remotely. In some embodiments, what constitutes an authorised type of patient transport apparatus may dynamically change based on input from a remote user or authorised personnel local to the vehicle, based on information input such as a type of condition the patient is being treated for. In some embodiments, if it is determined that the type of the patient transport apparatus is not an authorised type of patient transport apparatus, certain steps may be neglected. For example, it may save power/memory to not determine which means of access to the vehicle is substantially suitable for accessing the vehicle based on the type of the patient transport apparatus in the captured image if the patient transport apparatus is not authorised to access. In some embodiments the process 1400 may be resumed or restarted subject to an override event such as that discussed in the foregoing.

Figure 15:
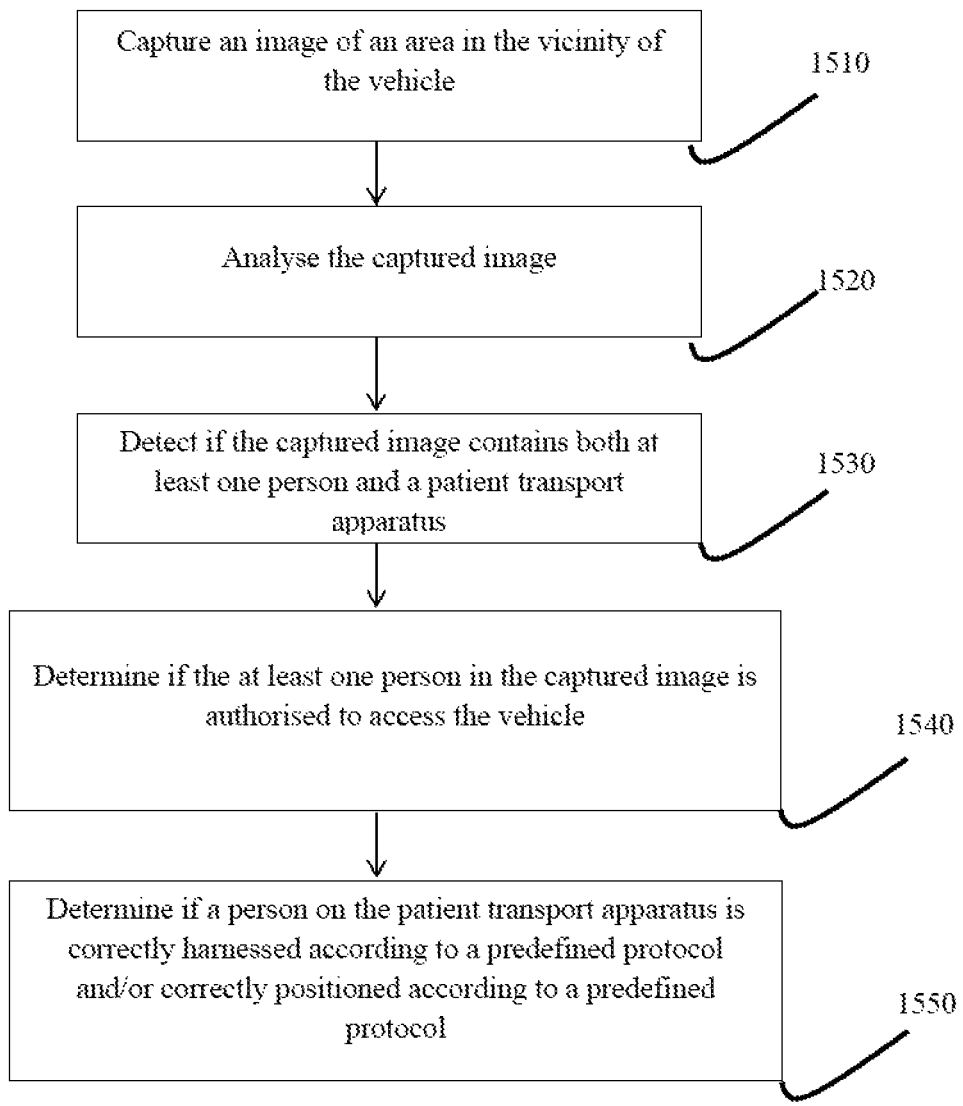
FIG. 15 is an illustration of an exemplary method according to an embodiment of the present disclosure.
Figure 16:
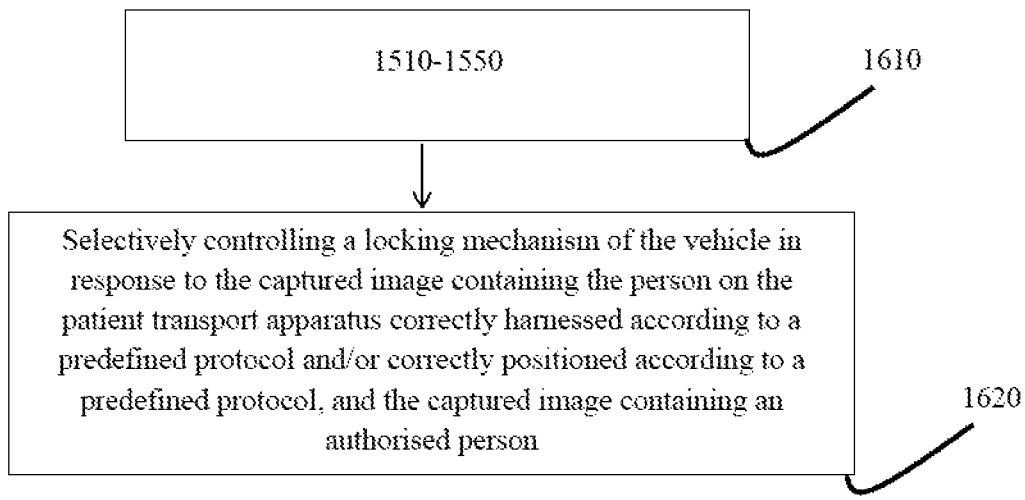
FIG. 16 is an illustration of an exemplary method according to an embodiment of the present disclosure.
Figure 17:
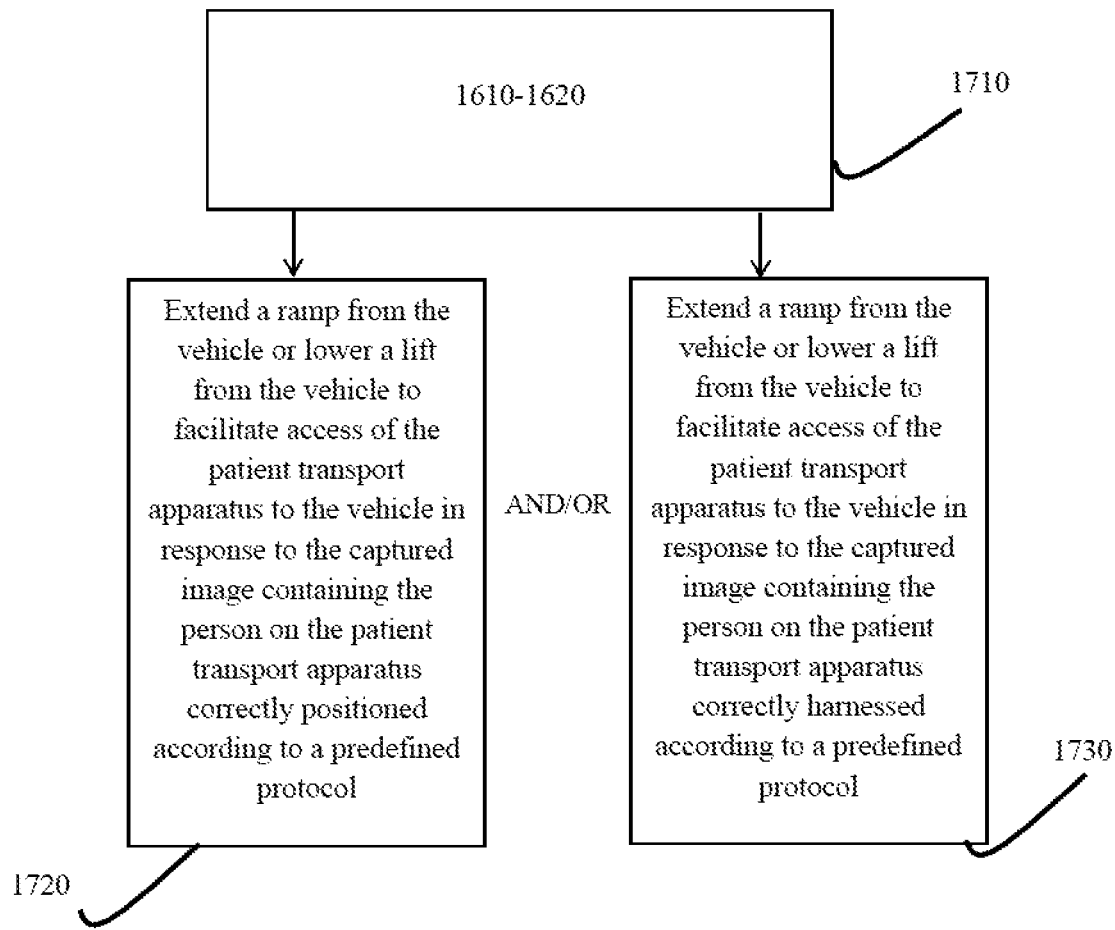
FIG. 17 is an illustration of an exemplary method according to an embodiment of the present disclosure.
Figure 18:
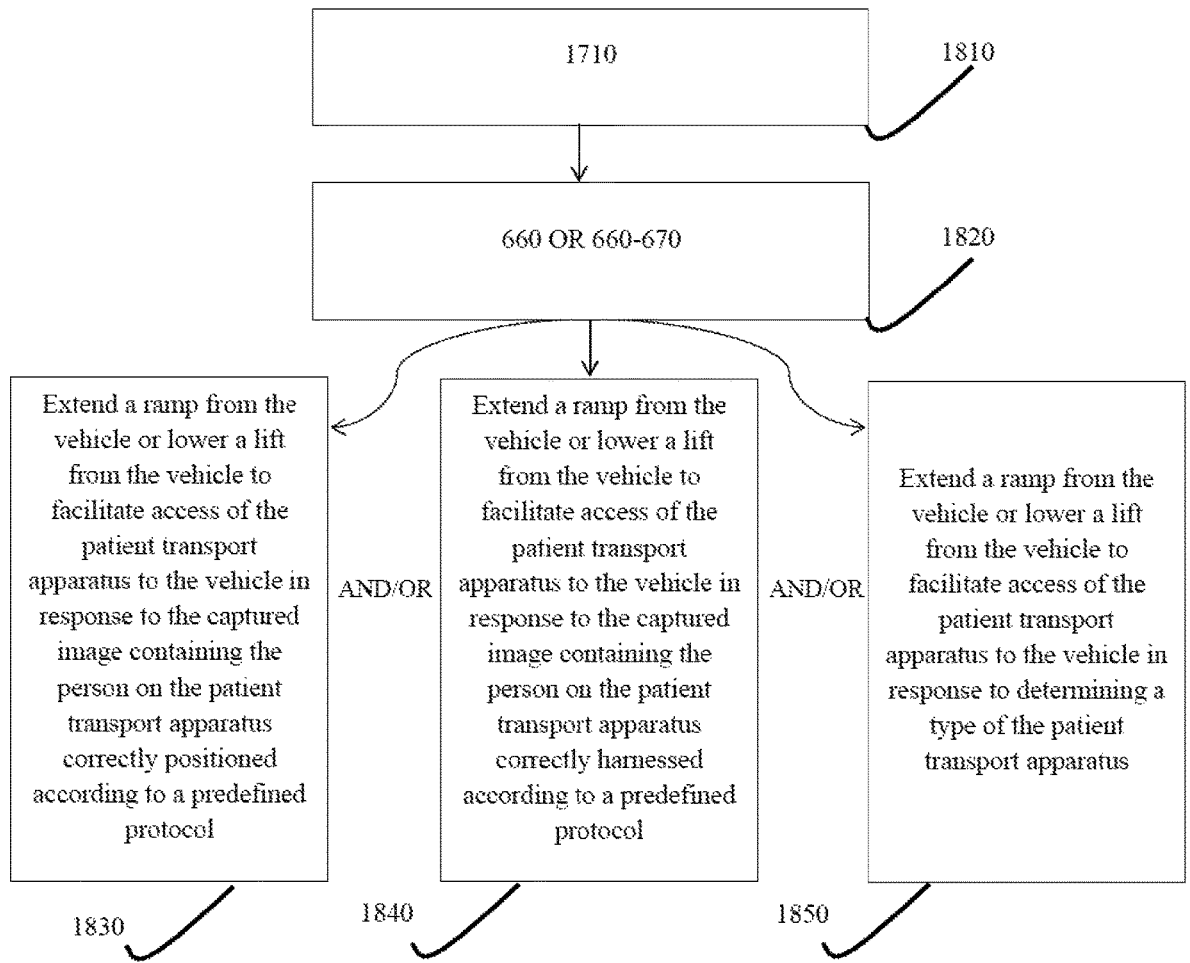
FIG. 18 is an illustration of an exemplary method according to an embodiment of the present disclosure.
Figure 19:
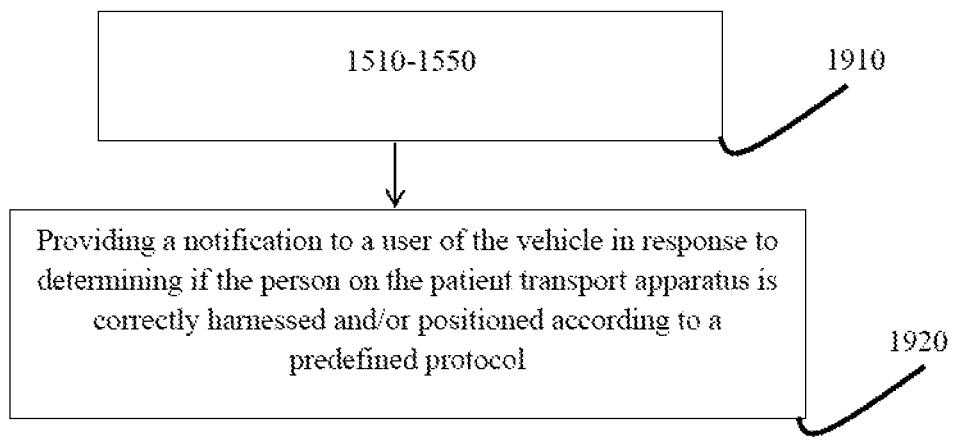
FIG. 19 is an illustration of an exemplary method according to an embodiment of the present disclosure.

FIGS. 15-19 illustrate various embodiments of processes for determining patient safety, with FIG. 15 including steps 1510, 1520, 1530, 1540 and 1550), FIG. 16 including steps 1610 and 1620, FIG. 17 including steps 1710, 1720 and 1730, FIG. 18 including steps 1810, 1820, 1830, 1840, and 1850, and FIG. 19 including steps 1910 and 1920. In addition to determining if a patient is harnessed correctly and/or positioned correctly on the patient transport apparatus, in some embodiments the image analysing means 115 may further be configured to determine if the patient transport apparatus is secured in place in the vehicle and/or secured on a vehicle access means (for example a vehicle lift or vehicle ramp).

With regard to FIG. 18, it will be understood that the 'and/or' clause at 1820 for the three options which can be nominally labelled 'A', 'B' and 'C' may include all permutations of these labels. Namely, 'A and/or B and/or C may have within its meaning here:

$A'$ and $B$ and $C' = \{ABC\}$;

$A'$ and $B$ or $C' = \{AB, C, AC\}$;

$A$ or $B$ or $C = \{A, B, C\}$;

$A$ or $B$ and $C = \{A, BC, AC\}$.

For completeness, A, B and C here refer to steps 1830; 1840; 1850 respectively.

Referring to FIG. 18, there are several advantages of determining 1820 the type of patient transport apparatus (660) and optionally additionally determining the sub-category of the patient transport apparatus (670). In one regard, determining the type of patient transport apparatus and possibly additionally the sub-type of the patient transport apparatus will facilitate increased accuracy in determining whether the patient is correctly harnessed and/or positioned in the patient transport apparatus, since harnessing and positioning protocols may vary between various patient transport apparatuses. Moreover, as discussed above, determining the type and possibly sub-type of patient transport apparatus allows one to determine whether a vehicle ramp or lift ought to be actuated in to operation, and to extend a ramp or lower a lift in response to the type of patient transport apparatus detected. Accordingly, improved patient safety, improved patient safety protocol adherence, reduced power consumption and improved time efficiency are advantages of the processes of FIG. 18.

FIG. 19 provides an exemplary method similar to that of FIG. 15, but including the additional step of providing 1920 a notification to a user of the vehicle that the patient is not correctly positioned and/or harnessed. It will be understood that the steps of FIG. 19 may be further combined in a number of variations with the steps of FIGS. 16-18. What is more, a notification may further be provided in response to one or more of:

i) determining if the patient transport apparatus is correctly secured on the vehicle lift according to a predefined protocol;

ii) determining if the patient transport apparatus is correctly secured on the vehicle ramp according to a predefined protocol: or iii) determining if the patient transport apparatus is correctly secured in the interior of the vehicle according to a predefined protocol Accordingly, the above determinations i)-iii) may comprise steps performed appropriately in combination with any of the processes of FIGS. 16-19.

It will be understood that while a number of exemplary embodiments of a method according to the present disclosure have been disclosed in FIGS. 4 and 6-10, other combinations of the method steps of FIGS. 4 and 6-10 are possible and are envisaged to be so by the inventors. For example, one might combine the steps 910-920 of FIG. 9 with step 720 of FIG. 7 or steps 820-830 of FIG. 8.

FIGS. 20-22 (including steps 2010, 2020, 2030, 2110, 2120, 2210, 2220, and 2230) depict embodiments for determining if one or more predefined sanitary protocols are satisfied in the vehicle or in the vicinity of the vehicle, providing notifications, and logging information.

The image capture device 175 may further comprise thermal imaging capabilities, and/or a separate thermal imaging device (not illustrated) may be fitted to the vehicle. The image capture device 175 and the thermal imaging device may be fitted to the interior of the vehicle and/or the exterior of the vehicle as desired. FIGS. 23-26 illustrate a number of example scenarios relating to thermal imaging data capture.

Figure 23:
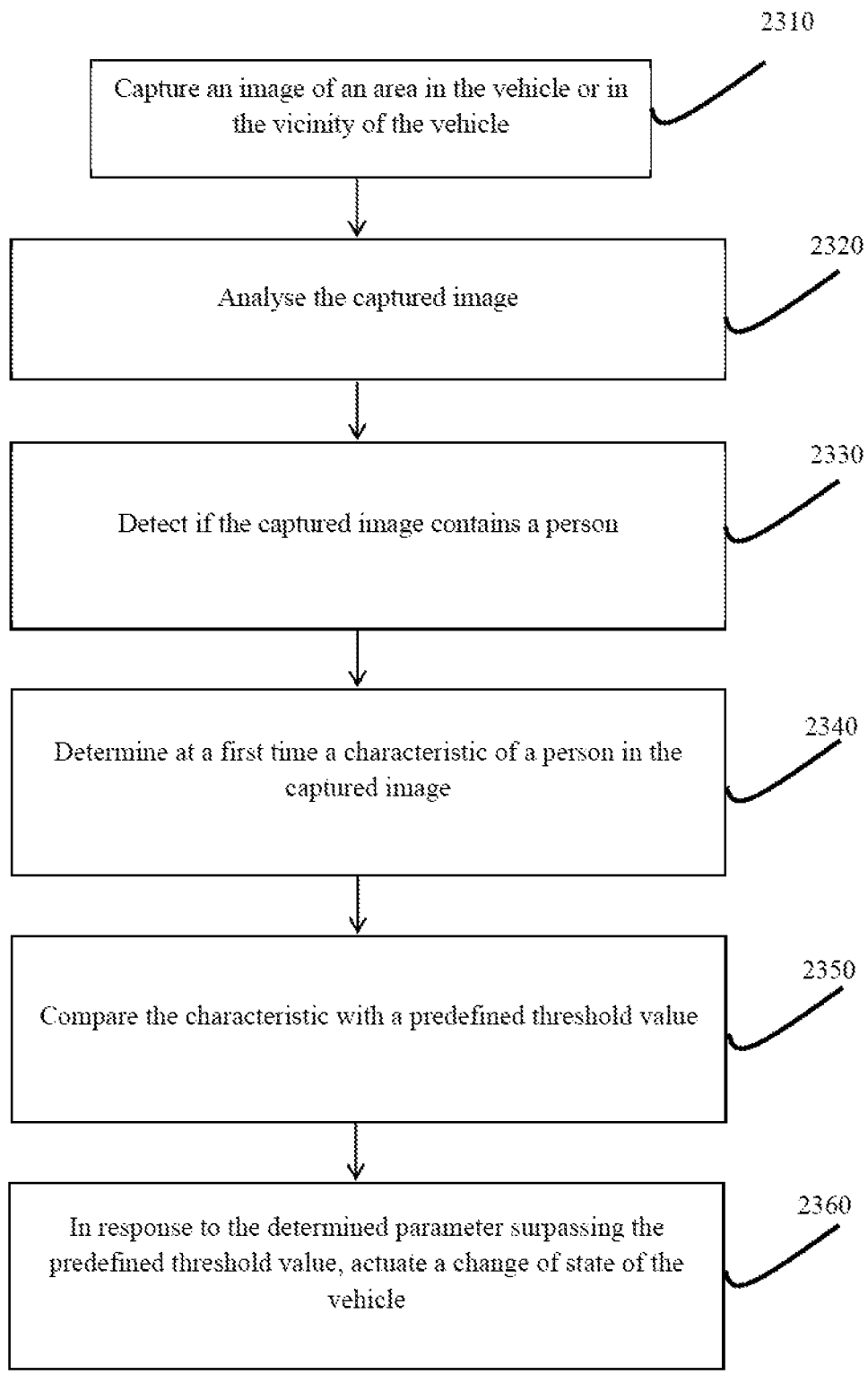
FIGS. 23-30 provide illustrations of exemplary methods according to various embodiments of the present disclosure.

Referring to FIG. 23, an image is captured in the vehicle or in the vicinity of the vehicle, 2310. The captured image is then analysed, 2320. A person is then detected in the captured image, 2330. A characteristic associated with the person is then determined at a first time, 2340. The determined characteristic is then associated with a predefined threshold value, 2350. In response to the characteristic surpassing the predefined threshold value, a change o state in the vehicle is actuated, 2360. In various embodiments, the subject may comprise a person, for example authorised or unauthorised personnel, or a patient. Temperature may be indicative of stress levels of persons in the vicinity of the vehicle, a critical event in a patient, or whether authorised personnel are fit to work in the vehicle. For example, if a threshold temperature of a patient is surpassed, this may indicate that a patient's condition has worsened. In various embodiments, actuating a change of state of the vehicle comprises one or more of: providing a notification to one or more areas of the vehicle: providing a notification to a user device: or creating a log in memory of an instance of the characteristic surpassing the predefined threshold value. It will be understood that the change of state may be actuated by a processing means in cooperation with other necessary components. For example the processing means may send instructions to the notification means to provide the notification in the vicinity of the vehicle, or the processing means may send instructions to a wireless transmission means to provide a notification to the user device.

Figure 24:
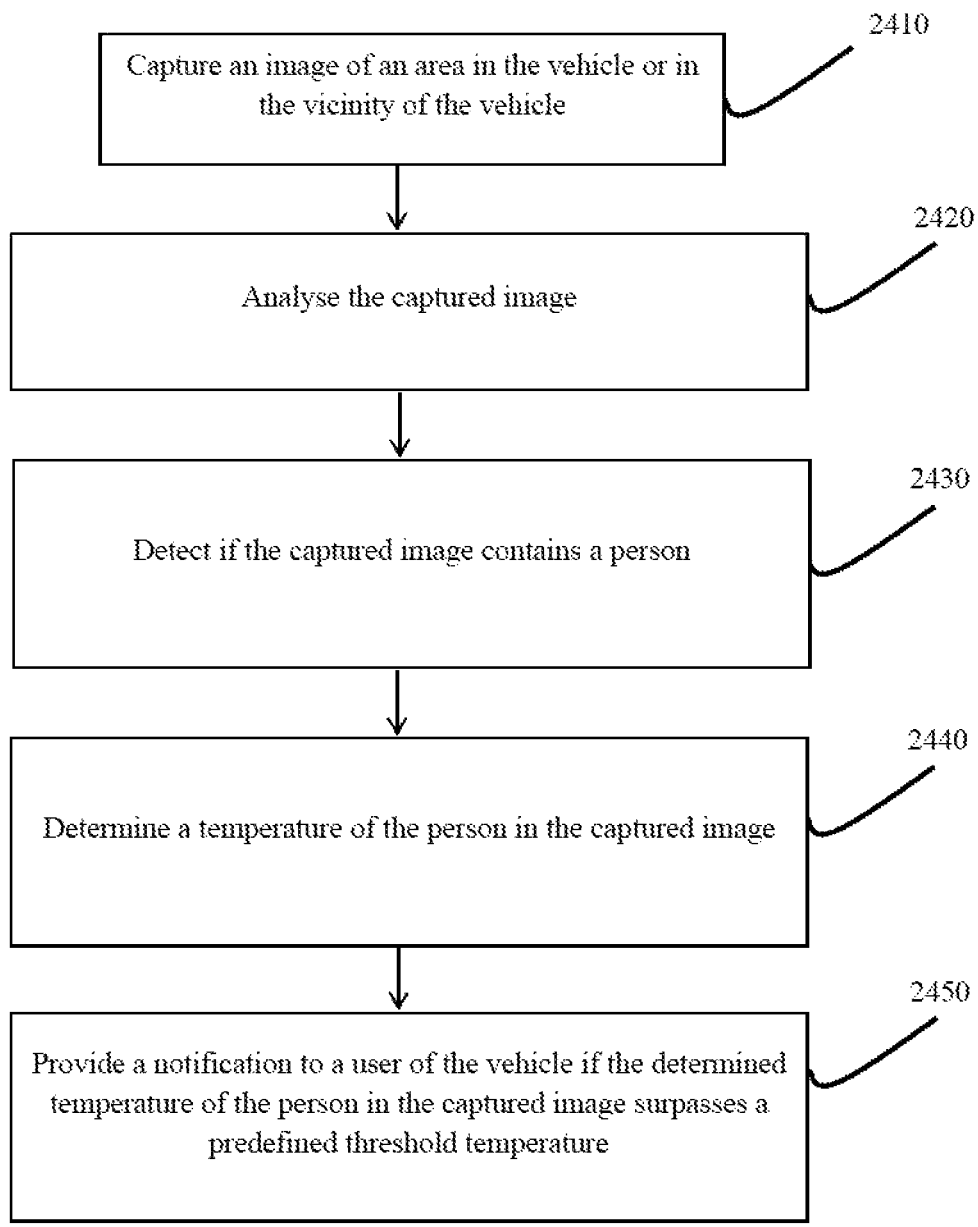

As illustrated in FIG. 24 (which includes steps 2410, 2420, 2430, 2440, and 2450), a notification may be provided to a user of the vehicle in response to the temperature of the subject being greater than a predefined threshold temperature at 2450. The notification may be provided in an audio and/or visual format. The notification may be provided to a user device such as a smart phone, or a tablet, or a system of the vehicle.

Captured thermal data such as temperature profiles in images may be fed in to a data processing application located locally or remotely such as in the cloud. In the exemplary embodiment the data processing application comprises a machine learning application. In some embodiments, in response to a predefined threshold value being surpassed the application may provide instructions to the vehicle environment control means to alter the temperature on board the vehicle to a particular value. In some embodiments the temperature on board the vehicle may be altered dynamically in response to thermal data captured in real time.

Figure 25:
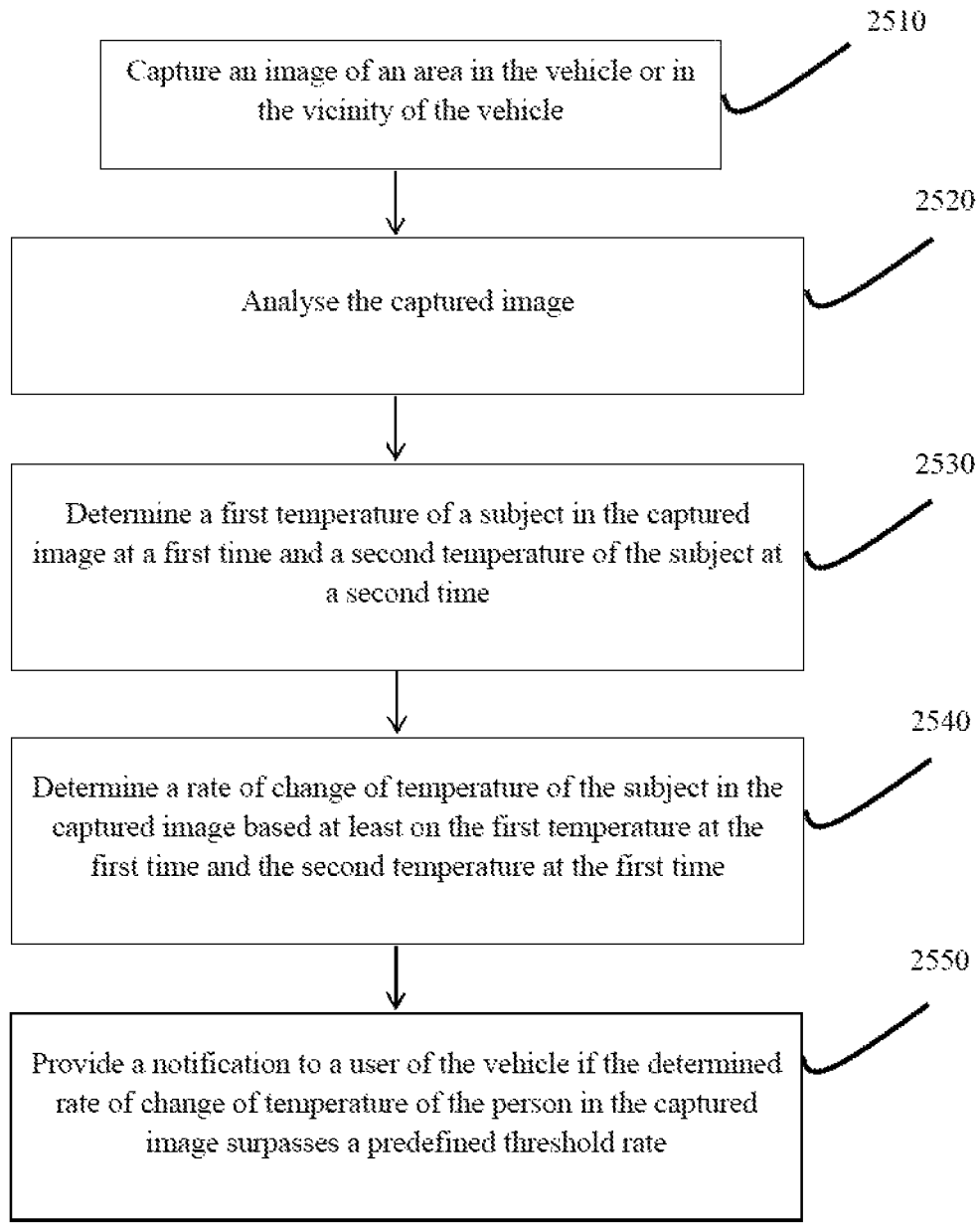
Figure 26:
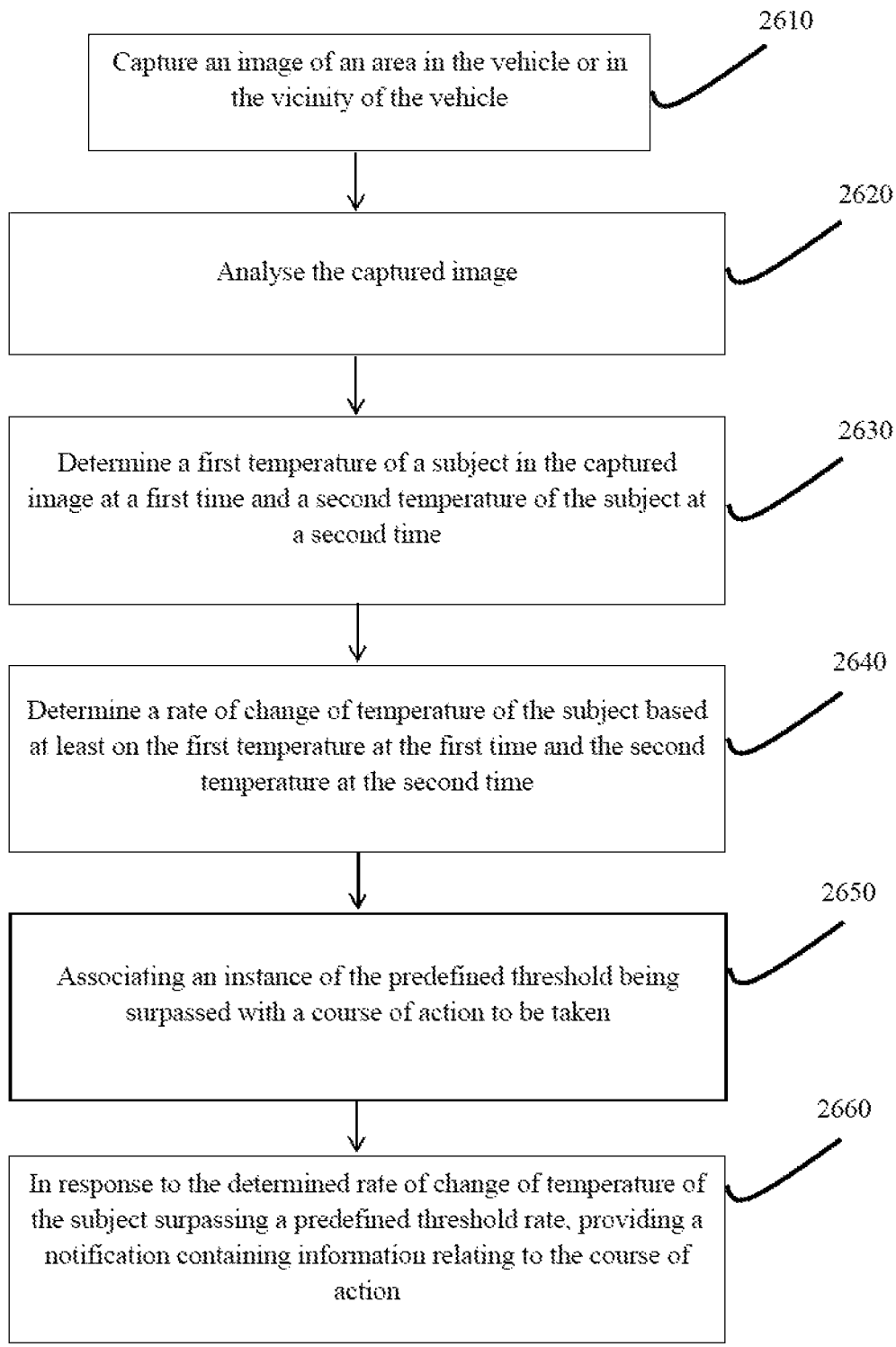

Referring to FIG. 25 (which includes steps 2510, 2520, 2530, 2540 and 2550), a first temperature of the subject in the captured image may be determined at a first time and a second temperature of the subject may be determined at a second time, 2510. A rate of change of the temperature of subject may then be determined based on the first temperature at the first time and the second temperature at the second time, 2520. Generally the temperature of a subject in captured image may be monitored in real time or at predefined intervals to monitor a rate of change of the temperature of the subject in the captured image. Similar to the above, a rate of change of temperature may be indicative of stress levels of persons in the vicinity of the vehicle, a critical event in a patient, or whether authorised personnel are fit to work in the vehicle. For example, if a threshold rate of change of temperature X/° C. of a patient is surpassed, this may indicate that a patient's condition has worsened. What is more, if a threshold rate of change of temperature X/° C. of a patient is surpassed, this may indicate that a patient is suffering for a particular condition/disease. For example, a temperature above the normal temperature of a human (approximately 37.5 degrees Celsius) may indicate a fever. A threshold temperature may be, for example, 37.8 degrees Celsius. If a person is suffering from a particular condition this may be used in determining a course of action such as quarantine or isolation of said person. In some embodiments it may be desirable to determine a rate of change of the rate of change of temperature (i.e. second order derivative). Referring to FIG. 26 (which includes steps 2610, 2620, 2630, 2640, 2650 and 2660), an event such as a threshold value of rate being surpassed may also be associated with a course of action to be taken, 2650. For example, the course of action may comprise one or more of: adjusting an ambient temperature of the interior of the vehicle, provision of medication to the person, or a change in vehicle speed. The notification means may provide a notification to a user of the vehicle or remotely located personnel containing information relating to the course of action, 2660. Such an event may also be recorded in local or remote memory. It will be understood that step 2650 may equally be performed in the method of FIGS. 23-25 or FIG. 27 ahead.

Notification of the changing condition of a patient may be indicative of whether a new course of action needs to be taken in relation to the patient. For example, whether certain drugs ought to be administered by paramedics, whether the current course of treatment is worsening the situation and/or whether the temperature in the interior of the vehicle needs to be altered. Notifications may be specifically directed to the driver of the vehicle, for example whether arrival at a hospital has become urgent or whether their driving is adversely affecting personnel and/or patient status.

Surface temperatures may be monitored in the interior or exterior of the vehicle. For example, a temperature of the surface of the patient transport apparatus may be monitored. Where the patient transport apparatus is exposed to a high or low temperature for a period of time, the surface of the patient transport apparatus may reach a temperature which is unsuitable for placing a patient thereon. In this case personnel may be notified appropriately.

A log of any thermal imaging data and related events may be recorded in local and/or remote memory for subsequent retrieval. Said data may form part of a report compiled by software. For example, said report may associate data with specific users of the vehicle.

Figure 27:
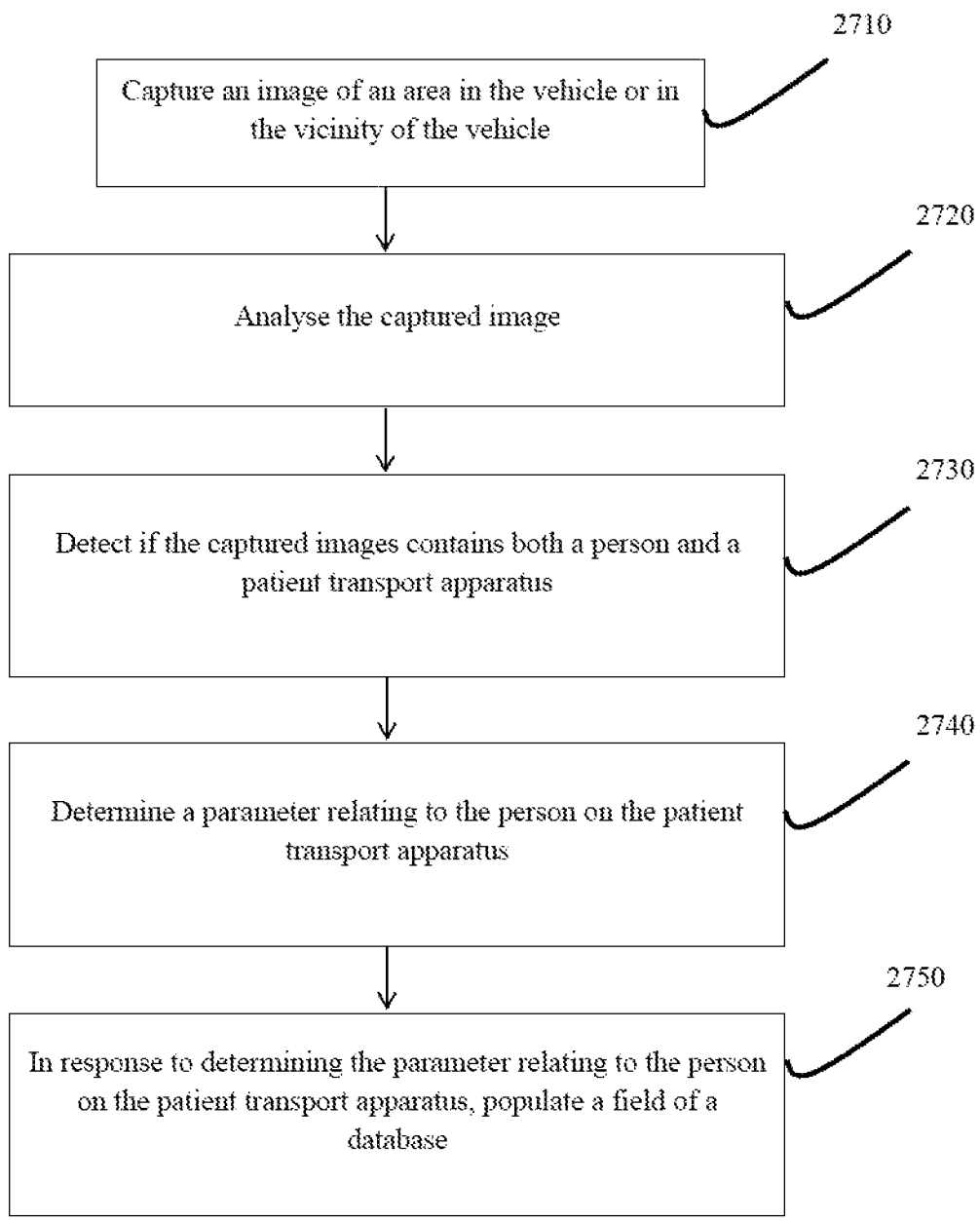

Referring now to FIG. 27, a method is provided according to an embodiment of the present disclosure. The method comprises capturing an image of an area in the vicinity of the vehicle, step 2710. The image is then analysed, step 2720. The image is analysed to detect if the captured image contains both a person and a patient transport apparatus, step 2730. The image is further analysed to determine a parameter relating to the person on the patient transport apparatus, step 2740. In response to determining the parameter relating to the person on the patient transport apparatus, a field of a database may be populated, step 2750. In the exemplary embodiment the database is an electronic patient care record (ePCR). In the exemplary embodiment the parameter relating to the person on the patient transport apparatus comprises a gender. Additional data parameters relating to the patient such as age, race, height and weight may also be estimated using machine learning algorithms or otherwise. It will be understood that any number of other captured data parameters described in the present disclosure may be used in appropriately populating a database such as the ePCR. The populated ePCR may be stored on local or remote memory for subsequent retrieval. The steps of the method of FIG. 27 may be implemented in combination with the method steps of other processes described herein. By way of example only, steps 2740 and 2750 may be implemented in combination with the steps of FIG. 4 or FIG. 6 or 10 and so on.

Figure 28:
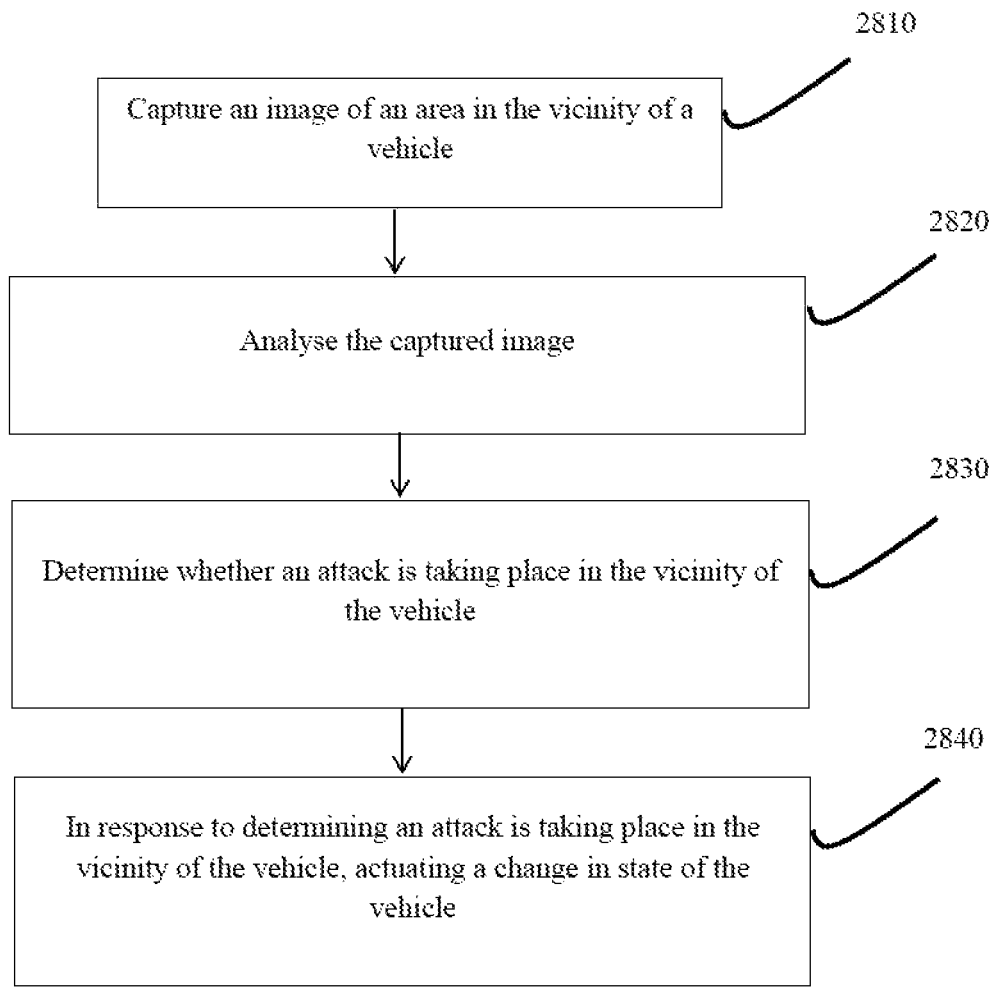

Referring to FIG. 28 there is provided a method of vehicle security. The method comprises capturing an image of an area in the vicinity of the vehicle, step 2810. The image is then analysed, step 2820. In a further step 2830, the method comprises determining whether an attack is taking place in the vicinity of the vehicle. In response to determining that an attack is taking place in the vicinity of the vehicle, a change of state of the vehicle is actuated, step 2840.

In various embodiments, actuating a change of state of the vehicle comprises one or more of: activating a recording mode of the image capture device(s) 175 in the interior and/or exterior of the vehicle: providing a notification to one or more areas of the vehicle: providing a notification to a user device: or creating a log of the attack event in memory. It will be understood that the change of state may be actuated by a processing means in cooperation with other necessary components. For example the processing means may send instructions to the notification means to provide the notification in the vicinity of the vehicle, or the processing means may send instructions to a wireless transmission means to provide a notification to the user device.

Figure 29:
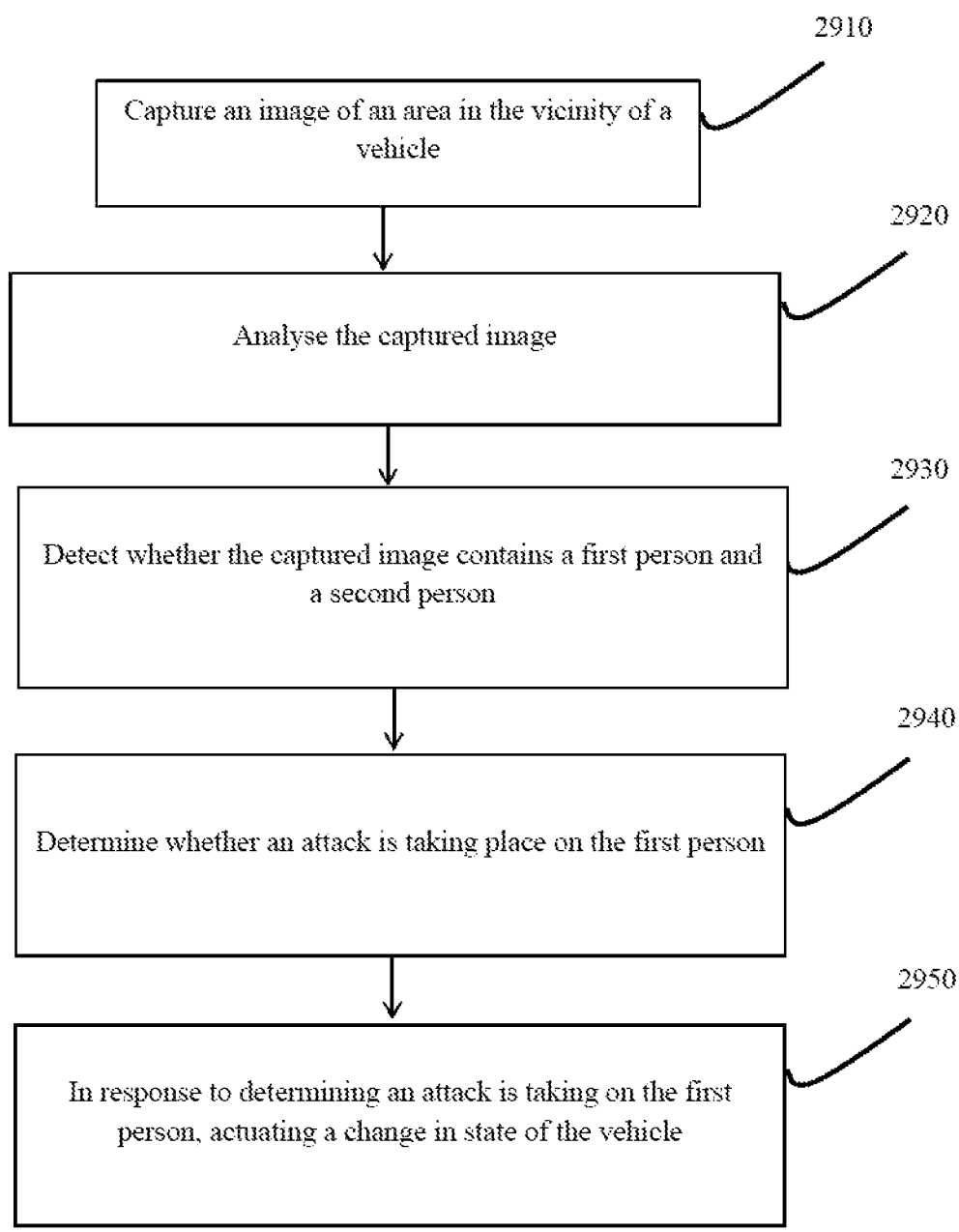

In various embodiments, determining whether an attack is taking place in the vicinity of the vehicle may comprise one or both of determining that an attack is taking place on the body of the vehicle, or on persons who are in the vicinity of the vehicle. For example, paramedics may be under attack near their ambulance, or police officers near their squad car. Accordingly, FIG. 29 illustrates a method including steps 2910 and 2920 and comprising the additional step of detecting a first person and a second person in the captured image, 2930. It is then determined whether an attack is taking place on the first person, 2940 and, if so, actuating a change in state of the vehicle 2950.

Figure 30:
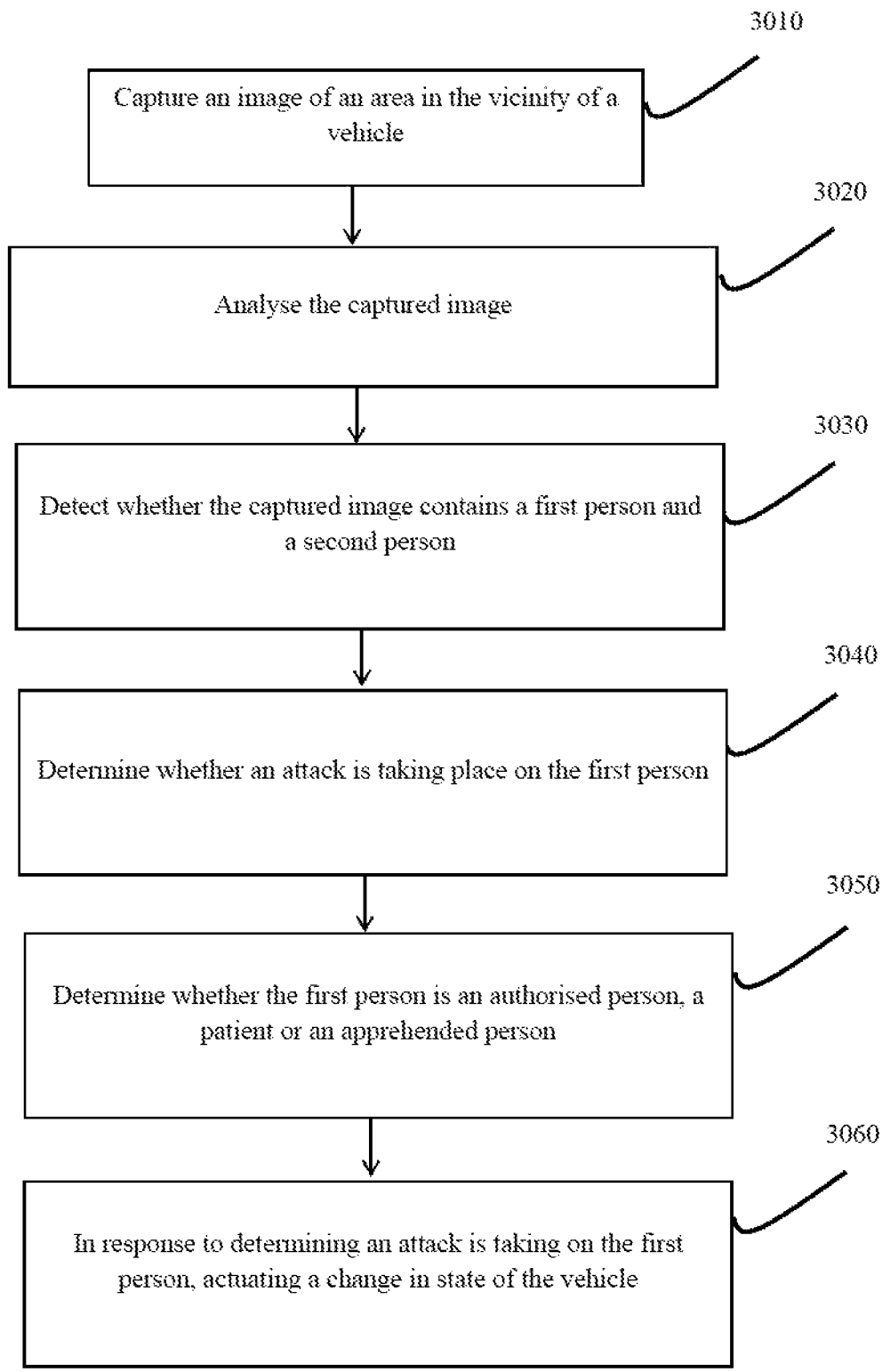

The first person may be an authorised person such as a paramedic or police officer, and the second person may be an assailant. The authorised personnel may be identified by their uniform, by facial recognition or by other means such as a scan-able code disposed on their clothing which can be compared to a database stored in memory. A person may be identified as a patient in numerous ways, for example based on their position and orientation such as on the ground or on a patient transport apparatus, based on being harnessed in to a patient transport apparatus, or based on certain medical equipment associated with them such as an IV drip. In the context of policing, a person may be identified as an apprehended person. This may be determined by the detection of the person as having their hands cuffed. A determination could thus be made by the image analysing means 115 that the cuffed individual is a person apprehended by an authorised person (i.e. a police officer). Identity information may be used in a report compiled after the incident. FIG. 30 provides a method including steps 3010, 3020, 3030, 3040, 3050 and 3060 in which the image analysing means 115 determines whether the first person is an authorised person, a patient or an apprehended person.

Determining that an attack is taking place may comprise detecting certain types of movement of the second person in the captured image. For example, detecting an arm of the second person in the captured image moving in a certain direction at a certain speed (i.e. a punch), or detecting a sequence of such events (a series of punches). The image analysing means 115 may be configured to execute the method of FIG. 28 implementing one or more machine learning algorithms. The machine learning algorithm(s) may be trained with examples of "attack behaviour" against which it can compare captured image data.

In the exemplary embodiment recording may continue until image analysing means 115 determines that the attack has ceased. When recording ends, the video data may be stored on local and/or remote memory for subsequent retrieval. Data such as but not limited to the identity of personnel involved in the incident, an ePCR of a patient involved in the incident, as well as time stamps, may be associated with the event.

Providing a notification to one or more areas of the vehicle may comprise activating an audibly and/or visually perceptible alarm on the exterior of the vehicle or in the driver's cab. The notification may continue until the image analysing means 115 determines that the attack has ended or until authorised personnel deactivate the notification. In the driver's cab, the notification may comprise a visual notification appearing on the user interface of the cab, and/or an audio notification emanating from audio speakers.

Providing a notification to the user device may comprise processor 105 sending instructions to a wireless transmission means to provide an audibly and/or visually perceptible alarm (e.g. sirens, flashing lights and the like), an automated email, push notification, a text message such as SMS, or other alert on a user device. The user device may comprise a device belonging to a safety officer. In some embodiments, the video may be live streamed to the safety officer's device for continual monitoring of the situation in real time.

In some embodiments, the method of FIG. 28 may further comprise controlling a locking mechanism of the vehicle in response to determining an attack is taking place in the vicinity of the vehicle.

It will be understood that the methods of FIGS. 28-30 may be extended to the detection and identification of additional persons in the captured image.

It will be understood that while exemplary features of an apparatus for actuating vehicle parameters using combined biometric personnel-authorised and patient transport apparatus-authorised access to the environment have been described, that such an arrangement is not to be construed as limiting the invention to such features. The method for detection of persons and objects and parameters related to both such as distance and velocity, and furthermore actuating the vehicle parameters and components, may be implemented in software, firmware, hardware, or a combination thereof. In one mode, the method is implemented in software, as an executable program, and is executed by one or more special or general purpose digital computer(s), such as a personal computer (PC: IBM-compatible, Apple-compatible, or otherwise), personal digital assistant, workstation, minicomputer, or mainframe computer. The steps of the method may be implemented by a server or computer in which the software modules reside or partially reside.

Generally, in terms of hardware architecture, such a computer will include, as will be well understood by the person skilled in the art, a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the other computer components.

The processor(s) may be programmed to perform the functions of the method for authorising persons and controlling vehicle parameters such as but not limited to the lock state of the doors and the state of access facilities such as a ramp or lift, or vehicle parameters such as but not limited to temperature. The processor(s) is a hardware device for executing software, particularly software stored in memory. Processor(s) can be any custom made or commercially available processor, a primary processing unit (CPU), an auxiliary processor among several processors associated with a computer, a semiconductor based microprocessor (in the form of a microchip or chip set), a macro-processor, or generally any device for executing software instructions.

Memory is associated with processor(s) and can include any one or a combination of volatile memory elements (e.g., random access memory (RAM, such as DRAM, SRAM, SDRAM, etc.)) and non-volatile memory elements (e.g., ROM, hard drive, tape, CDROM, etc.).

Moreover, memory may incorporate electronic, magnetic, optical, and/or other types of storage media. Memory can have a distributed architecture where various components are situated remote from one another, but are still accessed by processor(s).

The software in memory may include one or more separate programs. The separate programs comprise ordered listings of executable instructions for implementing logical functions in order to implement the functions of the modules. In the example of heretofore described, the software in memory includes the one or more components of the method and is executable on a suitable operating system (O/S).

The present disclosure may include components provided as a source program, executable program (object code), script, or any other entity comprising a set of instructions to be performed. When a source program, the program needs to be translated via a compiler, assembler, interpreter, or the like, which may or may not be included within the memory, so as to operate properly in connection with the O/S. Furthermore, a methodology implemented according to the teaching may be expressed as (a) an object oriented programming language, which has classes of data and methods, or (b) a procedural programming language, which has routines, subroutines, and/or functions, for example but not limited to, C, C++, Pascal, Basic, Fortran, Cobol, Perl, Java, and Ada.

When the method is implemented in software, it should be noted that such software can be stored on any computer readable medium for use by or in connection with any computer related system or method. In the context of this teaching, a computer readable medium is an electronic, magnetic, optical, or other physical device or means that can contain or store a computer program for use by or in connection with a computer related system or method.

Such an arrangement can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this disclosure, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. Any method descriptions or blocks in the Figures, should be understood as representing modules, segments, or portions of code which include one or more executable instructions for implementing specific logical functions or steps in the process, as would be understood by those having ordinary skill in the art.

The above detailed description of embodiments of the disclosure is not intended to be exhaustive or to limit the disclosure to the exact form disclosed. While specific examples for the disclosure are described above for illustrative purposes, those skilled in the relevant art will recognize various modifications are possible within the scope of the disclosure. For example, while processes and blocks have been demonstrated in a particular order, different implementations may perform routines or employ systems having blocks, in an alternate order, and some processes or blocks may be deleted, supplemented, added, moved, separated, combined, and/or modified to provide different combinations or sub-combinations. Each of these processes or blocks may be implemented in a variety of alternate ways. Also, while processes or blocks are at times shown as being performed in sequence, these processes or blocks may instead be performed or implemented in parallel or may be performed at different times. The results of processes or blocks may be also held in a non-persistent store as a method of increasing throughput and reducing processing requirements.

The invention claimed is:

1. A method comprising the steps of:
capturing an image of an area in the vicinity of a vehicle;
analysing the captured image;
detecting if the captured image contains a person;
determining at a first time a first temperature associated with the person in the captured image;
determining, at a second time, a second temperature associated with the person in the captured image;
determining a rate of change of temperature of the person based at least on the first temperature and the second temperature;
comparing the determined rate of change of temperature with a predefined threshold rate of change of temperature value; and
in response to the determined rate of change of temperature value surpassing the predefined threshold rate of change of temperature value, altering the ambient temperature on board the vehicle in real time.

2. The method of claim 1, further comprising:
determining that the determined rate of change of temperature exceeds the predefined threshold rate of change of temperature value;
identifying a course of action to be taken, wherein the course of action comprises at least one of: causing the provision of medication to the person, and causing a change in vehicle speed or acceleration.

3. The method of claim 1, further comprises providing, by a notification means, a notification to one or more areas of the vehicle in response to the determined rate of change of temperature surpassing the predefined temperature rate of change value, wherein the notification provided to the one or more areas of the vehicle comprises an audibly and/or visually perceptible alert.

4. The method of claim 1, further comprising providing a notification to a user device in response to the determined rate of change of temperature surpassing the predefined temperature rate of change value, wherein the notification provided to the user device comprises at least one of (i) instructions indicating a course of action, and (ii) at least one of an audibly perceptible alarm, a visually perceptible alarm, and a push notification.

5. The method of claim 1, further comprising creating a log in memory of an instance of the determined rate of change of temperature surpassing the predefined temperature rate of change value.

6. The method of claim 1, further comprising recording in memory time stamps associated with determined characteristics and/or a number of people at any one time in the vehicle.

7. The method of claim 1, wherein the analysing the captured image includes operating one or more machine learning algorithms.

8. A system, comprising:
an image capture device configured for capturing an image of an area in the vicinity of a vehicle;
an image analysing means configured for analysing the captured image, wherein the image analysing means is configured for detecting a person in the captured image, wherein the image analysing means is further configured to determine a first temperature associated with the person at a first time and a second temperature associated with the person at a second time;
a memory storing at least a first predefined temperature rate of change value; and
a processor configured to determine a rate of change of temperature of the person based at least on the first temperature and the second temperature, and compare the determined rate of change of temperature with the predefined threshold temperature rate of change value, wherein the processor is configured to adjust the ambient temperature on board the vehicle in real time in response to the determined rate of change of temperature surpassing the predefined threshold temperature rate of change value.

9. The system of claim 8, further comprising a notification means, wherein the processor is configured to send instructions to the notification means to provide a notification to at least a first area of the vehicle in response to determining that an attack is taking place in the vicinity of the vehicle, wherein the notification comprises at least one of an audibly and visually perceptible alarm.

10. The system of claim 8, further comprising a wireless transmission means, wherein the processor is configured to send instructions to the wireless transmission means to provide a notification to a user device, wherein the notification provided to the user device comprises at least one of an audibly perceptible alarm, a visually perceptible alarm, and a push notification.

11. The system of claim 8, wherein the processor is further configured to:
determine that the determined rate of change of temperature exceeds the predefined threshold temperature rate of change value; and
identify a course of action stored in a second memory, wherein the course of action comprises at least one of: (i) causing a provision of medication to the person, (ii) changing a speed of the vehicle, and (iii) changing an acceleration of the vehicle, wherein each of the memory and the second memory are at least one of (i) a local memory and (ii) a database.

12. The system of claim 8, wherein the processor is configured to create a log in record of an instance of the determined rate of change of temperature surpassing the predefined threshold temperature rate of change value.

13. The system of claim 8, wherein the image analysing means is further configured to determine a number of people in the captured image; and
wherein the processor is configured to activate at least one of a lighting means and an vehicle environmental control means of the vehicle in response to the determined number of people in the captured image being at least equal to one.

14. The system of claim 8, wherein the processor is further configured to record one or more time stamps associated with determined characteristics and/or a number of people at any one time in the vehicle.

* * * * *